United States Patent
Beechem et al.

(10) Patent No.: US 12,002,572 B2
(45) Date of Patent: Jun. 4, 2024

(54) METHODS, APPARATUSES, SYSTEMS AND DEVICES FOR MOBILE DIGITAL SPATIAL PROFILING OF PATHOLOGICAL SPECIMENS

(71) Applicant: NanoString Technologies, Inc., Seattle, WA (US)

(72) Inventors: Joseph M. Beechem, Eugene, OR (US); Dwayne Dunaway, Seattle, WA (US); Jaemyeong Jung, Bellevue, WA (US); Peter E. Schultz, Longmont, CO (US); Eliot Sosin, Mercer Island, WA (US); Grant Tremel, Seattle, WA (US)

(73) Assignee: NanoString Technologies, Inc., Seattle, WA (US)

( * ) Notice: Subject to any disclaimer, the term of this patent is extended or adjusted under 35 U.S.C. 154(b) by 432 days.

(21) Appl. No.: 17/413,674

(22) PCT Filed: Dec. 20, 2019

(86) PCT No.: PCT/US2019/068069
§ 371 (c)(1),
(2) Date: Jun. 14, 2021

(87) PCT Pub. No.: WO2020/132577
PCT Pub. Date: Jun. 25, 2020

(65) Prior Publication Data
US 2022/0076809 A1    Mar. 10, 2022

Related U.S. Application Data

(60) Provisional application No. 62/783,735, filed on Dec. 21, 2018.

(51) Int. Cl.
*G16H 30/00* (2018.01)
*G06V 10/20* (2022.01)
(Continued)

(52) U.S. Cl.
CPC .......... *G16H 30/40* (2018.01); *G06V 10/255* (2022.01); *G16H 70/60* (2018.01); *H04W 4/80* (2018.02); *G06F 2218/10* (2023.01)

(58) Field of Classification Search
CPC ......... G16H 30/40; G16H 70/60; H04W 4/80; G06V 10/255; G06F 2218/10
See application file for complete search history.

(56) References Cited

U.S. PATENT DOCUMENTS

| 5,650,844 A | 7/1997 | Aoki et al. |
| 6,788,359 B2 | 9/2004 | Lee et al. |

(Continued)

FOREIGN PATENT DOCUMENTS

| CN | 1357753 A | 7/2002 |
| CN | 201166604 Y | 12/2008 |

(Continued)

OTHER PUBLICATIONS

Cesano, et al., Abstract 1371: Spatially-resolved, multiplexed digital characterization of protein distribution and abundance in FFPE tissue sections, AACR 107th Annual Meeting, Apr. 16-20, 2016, 5 pages.

(Continued)

*Primary Examiner* — Khai M Nguyen
(74) *Attorney, Agent, or Firm* — COOLEY LLP

(57) ABSTRACT

Embodiments of the present disclosure are directed to a compact, mobile, digital spatial profiling (DSP) system, and associated apparatuses, devices and methods, which are configured to image one or more regions-of-interest (ROIs), and then using UV light to cleave, for example, oligos off antibodies in one or more ROIs ("photocleaving"), and collect the photocleaved oligos for later hybridization and counting.

19 Claims, 38 Drawing Sheets

(51) Int. Cl.
*G16H 30/40* (2018.01)
*G16H 70/60* (2018.01)
*H04W 4/80* (2018.01)

(56) References Cited

U.S. PATENT DOCUMENTS

| | | | |
|---|---|---|---|
| 6,972,892 | B2 | 12/2005 | DeSimone et al. |
| 7,036,946 | B1 | 5/2006 | Mosier |
| 9,703,171 | B2 | 7/2017 | Zhou et al. |
| 11,800,990 | B2 * | 10/2023 | White .................. A61B 5/0261 |
| 2006/0161287 | A1 | 7/2006 | Simonis |
| 2009/0086316 | A1 | 4/2009 | Kawahito |
| 2013/0260382 | A1 * | 10/2013 | Ghosh .................... G02B 21/33 435/6.12 |
| 2015/0219979 | A1 | 8/2015 | Zhou et al. |
| 2015/0378143 | A1 | 12/2015 | Auguste |
| 2016/0209635 | A1 | 7/2016 | Yan |
| 2017/0016909 | A1 | 1/2017 | Beechem et al. |
| 2018/0330510 | A1 | 11/2018 | Watanabe |
| 2020/0080060 | A1 * | 3/2020 | Matheu ................ C12N 5/0062 |

FOREIGN PATENT DOCUMENTS

| | | |
|---|---|---|
| CN | 101738618 A | 6/2010 |
| CN | 101915615 A | 12/2010 |
| CN | 201837458 U | 5/2011 |
| CN | 102564590 A | 7/2012 |
| CN | 103149180 A | 6/2013 |
| CN | 103743485 A | 4/2014 |
| CN | 103913419 A | 7/2014 |
| CN | 205403956 U | 7/2016 |
| CN | 106017680 A | 10/2016 |
| CN | 106352978 A | 1/2017 |
| CN | 107589078 A | 1/2018 |
| CN | 107850768 A | 3/2018 |
| CN | 108225282 A | 6/2018 |
| CN | 108332855 A | 7/2018 |
| JP | 2003241108 A | 8/2003 |
| JP | 2008009298 A | 1/2008 |
| JP | 2008029360 A | 2/2008 |
| JP | 2017092730 A | 5/2017 |
| JP | 2018031890 A | 3/2018 |
| JP | 2018529314 A | 10/2018 |
| WO | WO-2017015099 A1 | 1/2017 |
| WO | WO-2018218085 A2 | 11/2018 |
| WO | WO-2020132577 A1 | 6/2020 |

OTHER PUBLICATIONS

Chen, et al., An Augmented Reality Microscope for Real-time Automated Detection of Cancer, Google AI Healthcare, Google, Inc., posted Apr. 16, 2018, 19 pages, with Supplementary Data, Updated Aug. 12, 2019 in Nature Medicine, 21 pages.

Chenn, Wnt/β-catenin signaling in cerebral cortical development, Organogenesis, Apr. 2008, pp. 76-80.

Distribution of In Vitro Diagnostic Products Labeled for Research Use Only or Investigational Use Only. (n.d.). Food and Drug Administration, 2013, 12 pages; Retrieved from https://www.fda.gov/downloads/MedicalDevices/DeviceRegulationandGuidance/GuidanceDocuments/ucm376118.pdf.

Dubeau, et al., Southern Blot Analysis of DNA Extracted from Formalin-fixed Pathology Specimens, Cancer Research, Jun. 1986, pp. 2964-2969.

Goyal, et al., S100b as a Prognostic Biomarker in Outcome Prediction for Patients with Severe Traumatic Brain Injury, Journal of Neurotrauma, Jun. 2013, pp. 946-957.

Jeong, et al., Brain Inflammation and Microglia: Facts and Misconceptions, Exp Neurobiol., Jun. 2013, pp. 59-67.

Mallory, The Results of the Application of Special Histological Methods to the Study of Tumors, The Journal of Experimental Medicine, Sep. 1908, pp. 575-593. Retrieved from http://www.ncbi.nlm.nih.gov/pmc/articles/PMC2124540/.

Misharin, et al., Flow Cytometric Analysis of Macrophages and Dendritic Cell Subsets in the Mouse Lung, Am J Respir Cell Mol Biol, Oct. 2013, pp. 503-510.

Müller, et al., Expression of CD34 in Pulmonary Endothelial Cells in vivo, Pathobiology, 2002, pp. 11-17.

Mudanyali, et al., Integrated rapid-diagnostic-test reader platform on a cellphone, Lab Chip, 2012, pp. 2678-2686.

Walter, Placental pathologic changes in malaria. A histologic and ultrastructural study, The American Journal of Pathology, Dec. 1982, pp. 330-342. Retrieved from http://www.ncbi.nlm.nih.gov/pmc/articles/PMC1916118/.

Xu, et al., S100A9 promotes human lung fibroblast cells activation through receptor for advanced glycation end-product-mediated extracellular-regulated kinase ½, mitogen-activated protein-kinase and nuclear factor-κB-dependent pathways, Clinical and Experimental Immunology, Sep. 2013, pp. 523-535.

* cited by examiner

| Device Need | Constraint | Acceptable Range | Full DSP |
|---|---|---|---|
| High plex | Analyte quantity | >10 | <800 |
| Quantitative | Signal to Noise ratio | 90% | 95% |
| Spatial Information | Illumination Resolution | <1 mm | 10 µm |
| Non-destructive | Illumination time | <3 minutes | 4 seconds |
| | UV power density | >50 mW/cm$^2$ | 1 W/cm$^2$ |
| User Interface | Field of View | >2 cm$^2$ | --- |
| | Material Cost | <$1000 | >$100,000 |

Figure 1C

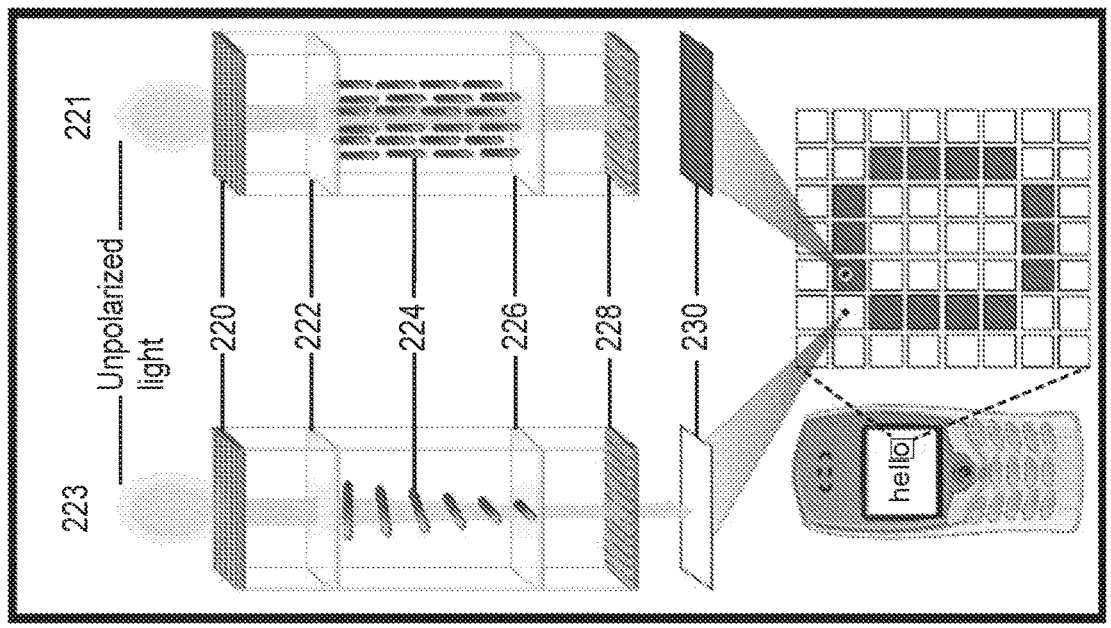
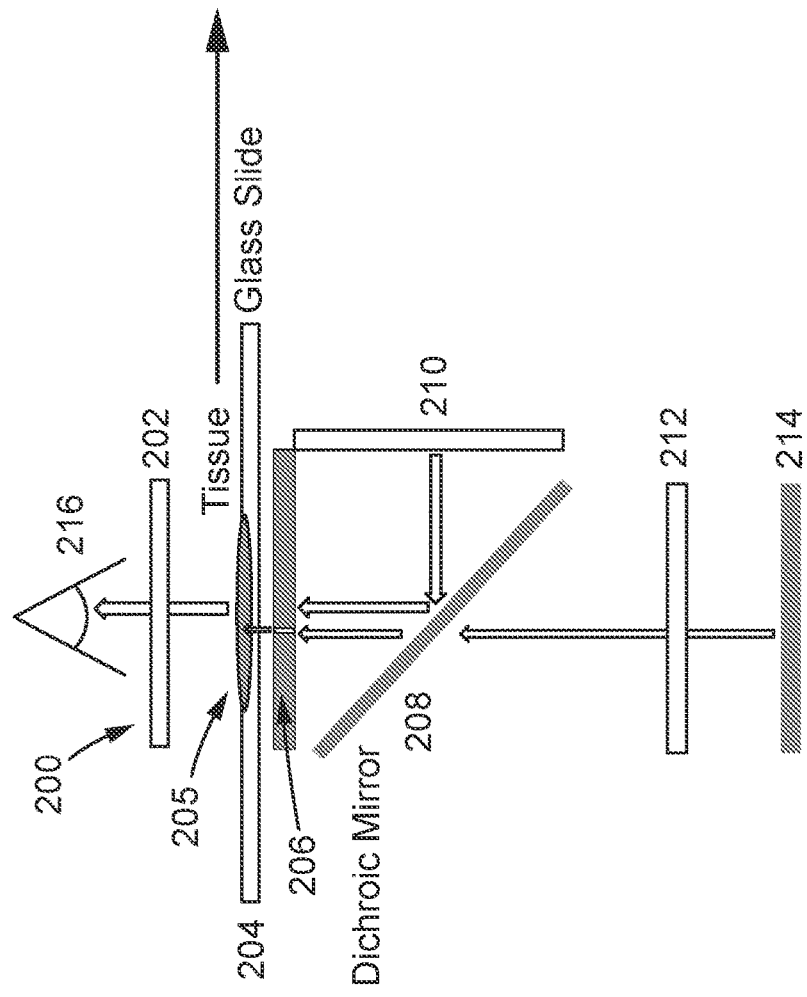
Figure 2A
Figure 2B

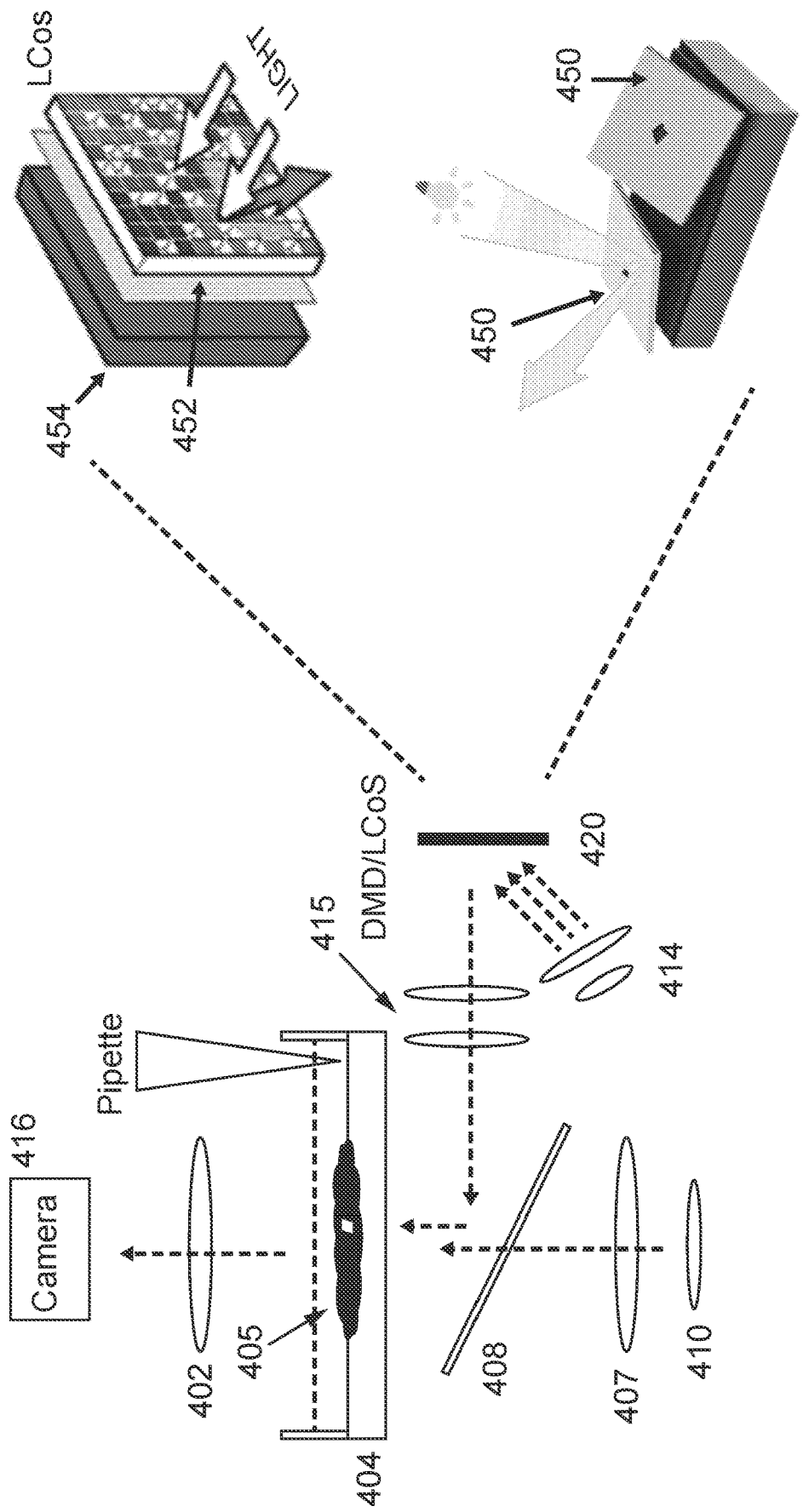

Four white dots on black
480

Four white corners on black
482

Cyan rectangle on white
484

486

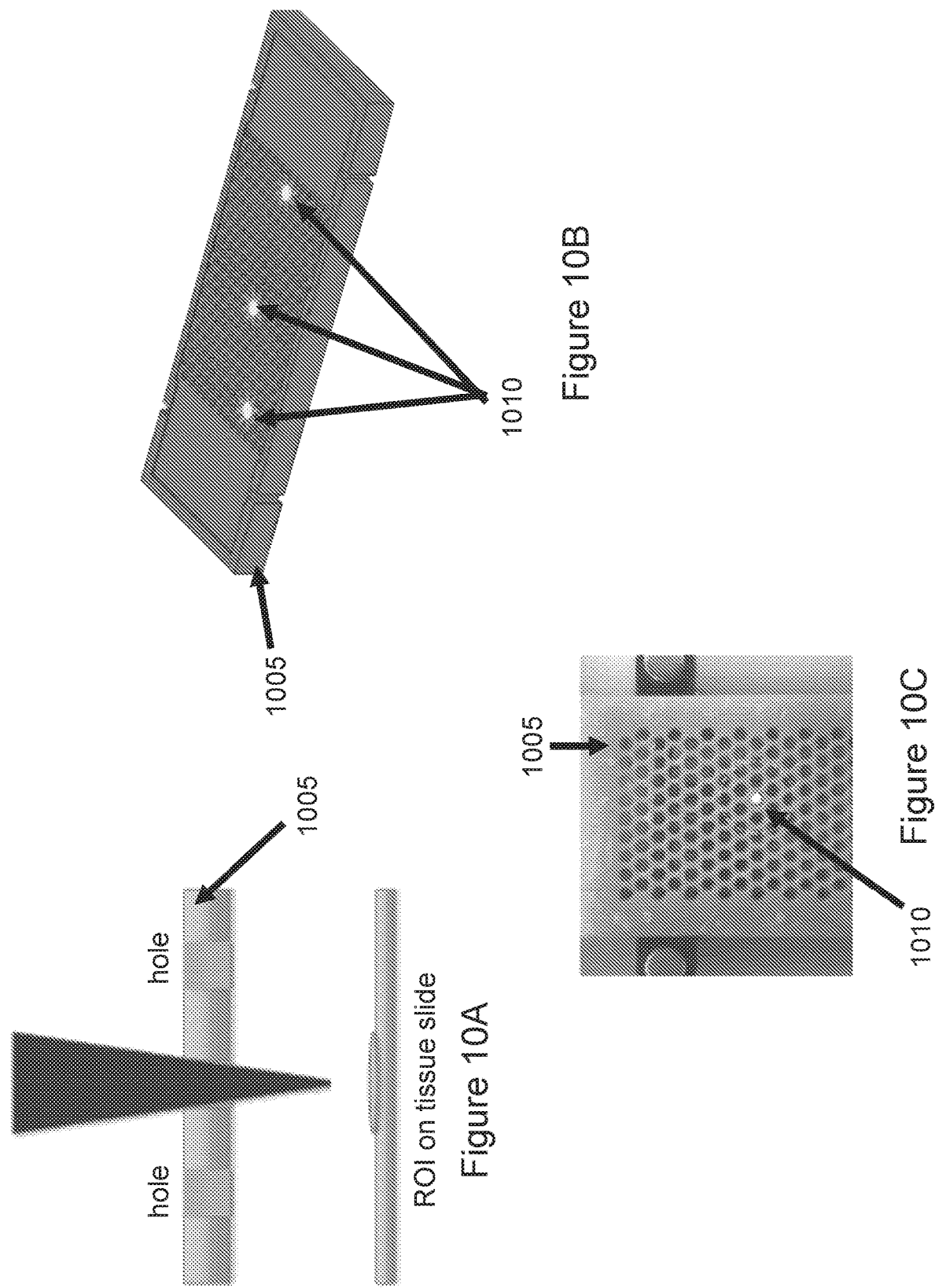

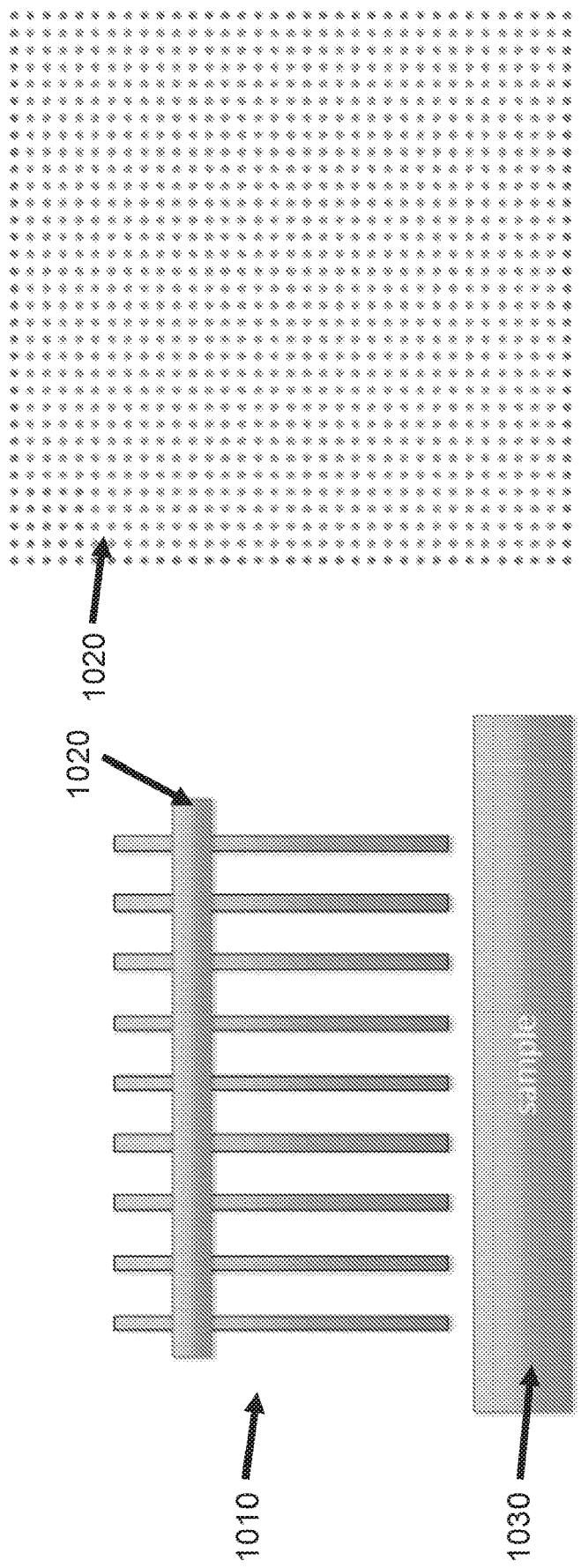

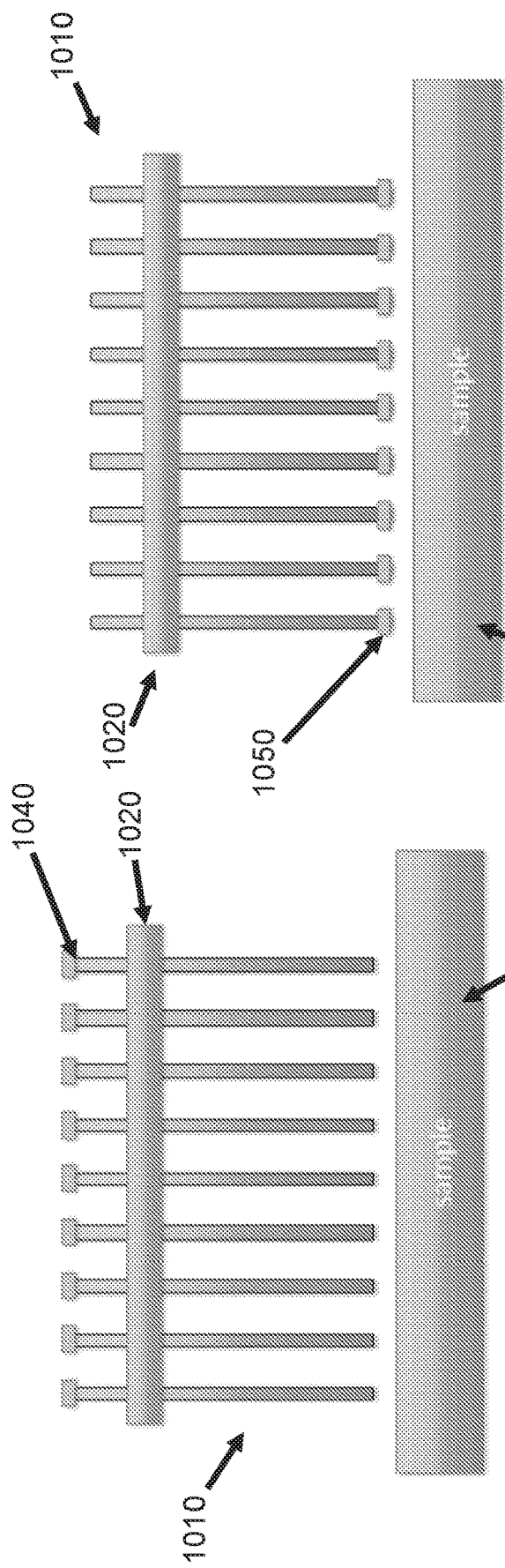

METHODS, APPARATUSES, SYSTEMS AND DEVICES FOR MOBILE DIGITAL SPATIAL PROFILING OF PATHOLOGICAL SPECIMENS

RELATED APPLICATIONS

This application is a U.S. National Phase application, filed under U.S.C. § 371, of International Application No. PCT/US2019/068069, filed Dec. 20, 2019, which claims benefit of and priority to U.S. provisional patent application No. 62/783,735, filed Dec. 21, 2019, the contents of each of are herein incorporated by reference in their entireties.

FIELD OF THE DISCLOSURE

Embodiments of the present disclosure relate to mobile digital spatial profiling for biochemical characterization of pathological specimens.

BACKGROUND

In biological research and clinical pathology, information of the spatial arrangement of biomolecules in tissues is critical to determining disease state and etiology. However, current methods are either "low-plex", that is, not quantitative, destructive, or lacking spatial information. To meet this need, digital spatial profiling (DSP) methods have been developed to quantify relative amounts of biological species in fixed tissue samples. Such methods target DNA, RNA, and proteins, and is, "high-plex," that is, the collection of an adequate (or greater) amount of information for determining a disease state and/or etiology, due to the use of a DNA-based fluorescent barcode. Each barcode is associated with an oligonucleotide bound to a molecular recognition moiety which can be cleaved using UV light and recovered in solution. The barcodes are then used to determine relative quantities of the molecules in the sample. While this method has many advantages, there is room in the market for a lightweight alternative.

SUMMARY OF SOME OF THE EMBODIMENTS

Embodiments of the present disclosure are directed to a reduced size, digital spatial profiling (DSP) system, and associated apparatuses, devices and methods. All of the preceding can be configured to image one or more regions-of-interest (ROIs) of a tissue, use UV light to cleave oligos (i.e., oligomer) off antibodies in one or more ROIs ("photo-cleaving"), and collect the photo-cleaved oligos, which can later be hybridized and counted (using, for example Nanostring® nCounter technology). In some embodiments, such functionality can also be provided in a mobile, and moreover (in some embodiments), a compact, form.

Accordingly, in some embodiments, such a compact, mobile DSP system can comprise, a housing, or other structure for containing at least one component of the DSP system, including, for example, a power source, a processor, a UV source (UVS), a visible light source (VLS) for bright field imaging such as, for example, an LED, LED array, fluorescence bulb, incandescent bulb, arc lamp, metal halide lamp, photomasking means configured to selectively illuminate a tissue sample with UV light from the UV source and/or visible light from the visible light source, a chamber configured to receive at least a portion of the slide having the tissue thereon, where the chamber can be configured with a liquid environment for tissue, and optic means (which in some embodiments could be provided outside the chamber) configured to at least one of direct and/or focus the UVS and/or VLS onto at least one of the tissue, slide, the chamber, the photomasking means, and a camera sensor operably linked to a personal mobile computing device (PMD). A PMD can include a phone, tablet, laptop and desktop. The operably linked camera sensor may be internal or integral to the PMD or external to the PMD. At least one of the housing and chamber is configured for removable attachment to the PMD such that the camera sensor can image the tissue.

Such embodiments may additionally include at least one or more of the following features, structures, functionality, steps, and/or clarifications (in some embodiments, a plurality thereof, an in further embodiments, all of), yielding yet further embodiments:

the photomasking means can comprise an LCD optionally having a backlight the VLS can comprise the LCD backlight or a separate external visible light source;

the optics means can comprise a first set for the UVS, which can include at least one of, a plurality of, or all of: a condenser lens, a scan lens, a dichroic mirror, and a second set of optics which can comprise an objective lens;

the dichroic mirror can be configured to redirect light from multiple sources into one optical axis;

the photomasking means can comprise an LCD configured as a programmable aperture so as to structure at least one of UV and visible light to reach the tissue only in a regions-of-interest (ROI);

the chamber can include a slot configured for receiving the/a slide;

the photomask can comprise at least one of: a digital micro-mirror device (DMD), a liquid crystal on silicon (LCoS) display, an organic light-emitting diode (OLED), a micro light-emitting diode (µLED) array, a fiber optic bundle, a liquid crystal displays (LCD), a scanning laser, and, a physical barrier;

the photomasking means can comprise an LCD including a pixel grid, and wherein the LCD is arranged at a predetermined distance from the tissue, where:
the predetermined distance can be configured such that the tissue is not obscured by the pixel grid;
the predetermined distance can be between approximately 0.01 to 5 mm;
the predetermined distance can be between approximately 0.50 to 2.5 mm;
the predetermined distance can be between approximately 0.75 to 2.25 mm; or
the predetermined distance can be between approximately 1 to 2 mm; and/or
the predetermined distance can be configured to at least provide clear visualization
of tissue, or to minimize diffusion of UV light;

the photomasking means can be configured to provide at least one of: an illumination resolution of between approximately 50 and 300 nm, a field of view between approximately 1-12.5 cm² or 5-12.5 cm², and/or a magnification of between approximately 1-5× or 1-3×;

at least one of the housing, chamber, and slot are configured to enable the slide to move relative thereto, where:
relative movement of the slide can be configured for tissue imaging;

at least one of the housing, the chamber and the slot is configured to receive and/or retrieve at least one solution, where receiving and/or retrieving of the at least one solution can be via fluid transport, where fluid transport can comprise at least one of pipetting and capillary action, and pipetting may be either manual or automatic via robotic means;

the housing can comprise or include at least one of, in some embodiments, a plurality of, and in some embodiment, all of: a plurality of scaffolds, a PMD frame, at least one objective lens frame, at least one slide frame, a photomasking frame, at least one condenser frame, and at least one thermal management means;

the thermal management means can comprise at least one of a heat sink, a heat pump, a fan, a liquid cooling system, and a Peltier device;

the housing can be configured to removably receive a single objective lens frame of a plurality of objective lens frames, where each has a different objective lens and corresponding magnification, where:

each objective lens frame can be configured so as to provide a different spacing from the camera sensor; and/or the at least thermal management means can comprise a plurality of heatsink clips;

further may include the PMD;

the PMD can include at least one of, and in some embodiments, a plurality of, and in some embodiments, all of: a PMD processor, a display, the camera sensor for imaging the tissue arranged on the slide, and first wireless communication means for communicating information to a remote device either directly or via a network, and optionally second wireless communications means for communication with a local device; and/or the second wireless communications means can comprise at least one of Bluetooth, Wi-Fi or infra-red;

a software application, which can be configured to operate on the processor, which can be configured to cause the mobile device to display a graphical-user-interface (GUI), the GUI can be configured to receive user input to select a/the region-of-interest (ROI) of a tissue image obtained via the camera sensor of the tissue slide and presented on a/the display of the PMD;

the system can be further configured for at least one of dark-field microscopy, bright-field microscopy, phase-contrast microscopy, fluorescent microscopy and microscopy with ultraviolet surface excitation;

a pump system configured to provide a flow of a solution to the slide, where the solution can be a buffer and/or tissue stain;

a temperature sensor which can be configured to determine the temperature in at least one of the housing and chamber;

a/the processor can be configured to:

receive input from the temperature sensor corresponding to a sensed temperature, and/or to at least one of: turn off the UVS upon the sensed temperature being greater than a predetermined temperature; and provide at least one of a visual and audible warning upon the sensed temperature being greater than a predetermined amount;

sealing means which can be configured to maintain a liquid environment over the tissue; and manual fluid collection guiding means which can:

be arranged proximate the issue, be configured to enable pipetting solution from the tissue, and comprise a grid barrier where the grid barrier can be configured within or proximate to the sealing means or can be configured as or with a flow cell and/or the grid barrier can be arranged within or proximate to the chamber.

In some embodiments, the manual fluid collection guiding means can comprise a microarray where the microarray can be configured as or with a flow cell and/or the microarray can be arranged within or proximate to the chamber.

In some embodiments, a digital spatial profiling system is provided and comprises at least one of, and in some embodiments, a plurality of, and in some embodiments, all of: a personal mobile device (PMD) having a processor, a display, a camera sensor for imaging a tissue arranged on a slide, and communication means for communicating information to a remote device either directly or via a network, a software application operating on the processor and configured to cause the mobile device to display a graphical-user-interface (GUI) configured to receive user input to select a region-of-interest (ROI) of a tissue image obtained via the camera sensor of the tissue slide and presented on the display, and a housing or other structure for containing at least one component of the DSP system including, which can include at least one of, and in some embodiments, a plurality of, and in some embodiments, all of: a UV source (UVS), a visible light source (VLS) for bright field imaging, photomasking means configured to selectively illuminate the tissue with UV light from the UV source or visible light from the visible light source, a slot configured to receive the slide, and a chamber configured to receive at least a portion of the slide having tissue thereon via the slot. The chamber can be configured with aqueous environment for tissue. The system may also include optic means configured to at least one of direct and/or focus the UVS and/or VLS onto at least one of the tissue, the chamber, the photomasking means, and the camera sensor. The housing, slot, and/or chamber can be configured for removable attachment to the PMD such that the camera sensor can image the tissue, and the communication means can be a wireless communication means.

In some embodiments, a digital spatial profiling (DSP) method is provided and includes at least one of, and in some embodiments, a plurality of, and in some embodiments, all of: optionally providing a system, apparatus, and/or device according to of such disclosed systems, apparatuses and devices, initiating the software application on the/a personal mobile device (PMD), inserting a slide with a tissue sample, the tissue having previously been conjugated with an antibody solution and prior to insertion, covered in a buffer solution, such that it is received by the chamber for imaging and aligned with the photomask, providing illuminating light to the tissue, imaging the tissue sample with the camera sensor of the PMD and displaying the image via the PMD display, selecting a plurality of markers of the photomask displayed via the GUI, such selection forming an outline of a rectangle, selecting a ROI via the GUI, wirelessly connecting the PMD to the DSP system, ceasing illuminating light, exposing the tissue to UV illumination for a predetermined period of time sufficient to cleave oligos in the tissue, and collecting the solution from the tissue containing cleaved oligos.

Such embodiments, may additionally include at least one or more of the following features, structures, functionality, steps, and/or clarifications (in some embodiments, a plurality thereof, an in further embodiments, all of), yielding yet further embodiments:

imaging the photomask prior to inserting the slide so as to calibrate the photomask, and changing the size of the rectangle outlined by the selected markers, where the changed sizes can correspond to one of a plurality of designated sizes.

In some embodiments, a non-transitory computer readable medium is provided, having stored thereon instructions for enabling one or more computer processors to conduct one or more steps of any of the method embodiments presented by the present disclosure.

In some embodiments, the first wireless communication means for communicating information to a remote device either directly or via a network allows for the remote selection of ROIs and/or the delivery of healthcare services, such as health assessments or consultations, over the telecommunications infrastructure.

These and other embodiments of the present disclosure will become even clearer with reference to the figures, a brief description of which is provided below, and additional details of at least some embodiments of the disclosure which follows.

BRIEF DESCRIPTION OF THE FIGURES

FIG. 1B-2 illustrates a schematic of a DSP system according to some embodiments of the present disclosure;

FIG. 1C is a chart of design considerations for DSP systems, according to some embodiments;

FIG. 2A is a schematic of at least a portion of a DSP system according to some embodiments of the present disclosure;

FIG. 2B is a schematic of an LCD masking component representing a portion of a DSP system according to some embodiments of the present disclosure;

FIG. 2C-1 is a schematic of at least a portion of a DSP system according to some embodiments of the present disclosure;

FIG. 2C-2 is a schematic of at least a portion of a DSP system according to some embodiments of the present disclosure;

FIG. 2C-3 is a schematic of at least a portion of a DSP system according to some embodiments of the present disclosure, illustrating use of a UV LED component of the system;

FIGS. 2E-1 through 2E-5 illustrate sealing functionality, and pipetting fluid in/out of a slide for a DSP system according to some embodiments of the present disclosure;

FIGS. 4A and 4B, are schematics which illustrate a digital micro-mirror device (DMD/liquid crystal on silicon (LCoS)), reflective mask structure and operation, according to some embodiments of the present disclosure;

FIGS. 10A-10E-4 illustrates examples of fluid transport to/from a slide and/or an assay (e.g., 96 well plate), according to some embodiments of the present disclosure.

DETAILED DESCRIPTION FOR AT LEAST SOME OF THE DISCLOSED EMBODIMENTS

Some embodiments of the present disclosure provide for a compact, mobile, digital spatial profiling (DSP) systems (as well as associated apparatuses, devices, and methods) are provided, and are configured to image one or more regions-of-interest (ROIs), use UV light to cleave oligos off antibodies in each ROI ("photo-cleaving"), and collect the photo-cleaved oligos (for later hybridization and counting using, for example nanostring® nCounter technology). Some such embodiments of the present disclosure are further to design considerations for DSP systems as illustrated in the chart of FIG. 1C.

Figure 1A:
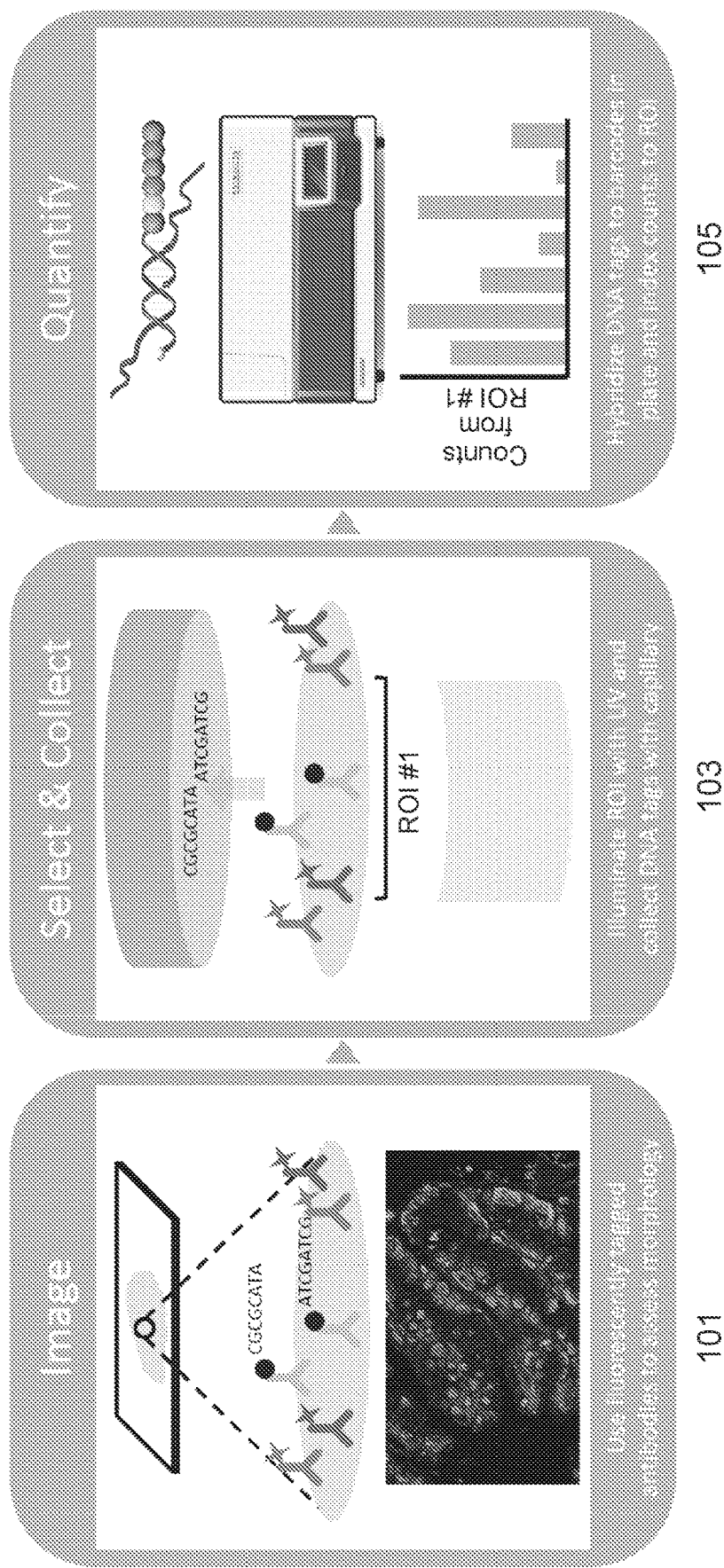
FIG. 1A illustrates a schematic of an overview of some of the steps performed by a compact, mobile, digital spatial profiling (DSP) system, according to at least some embodiments of the present disclosure.
Figures 1, 1B:
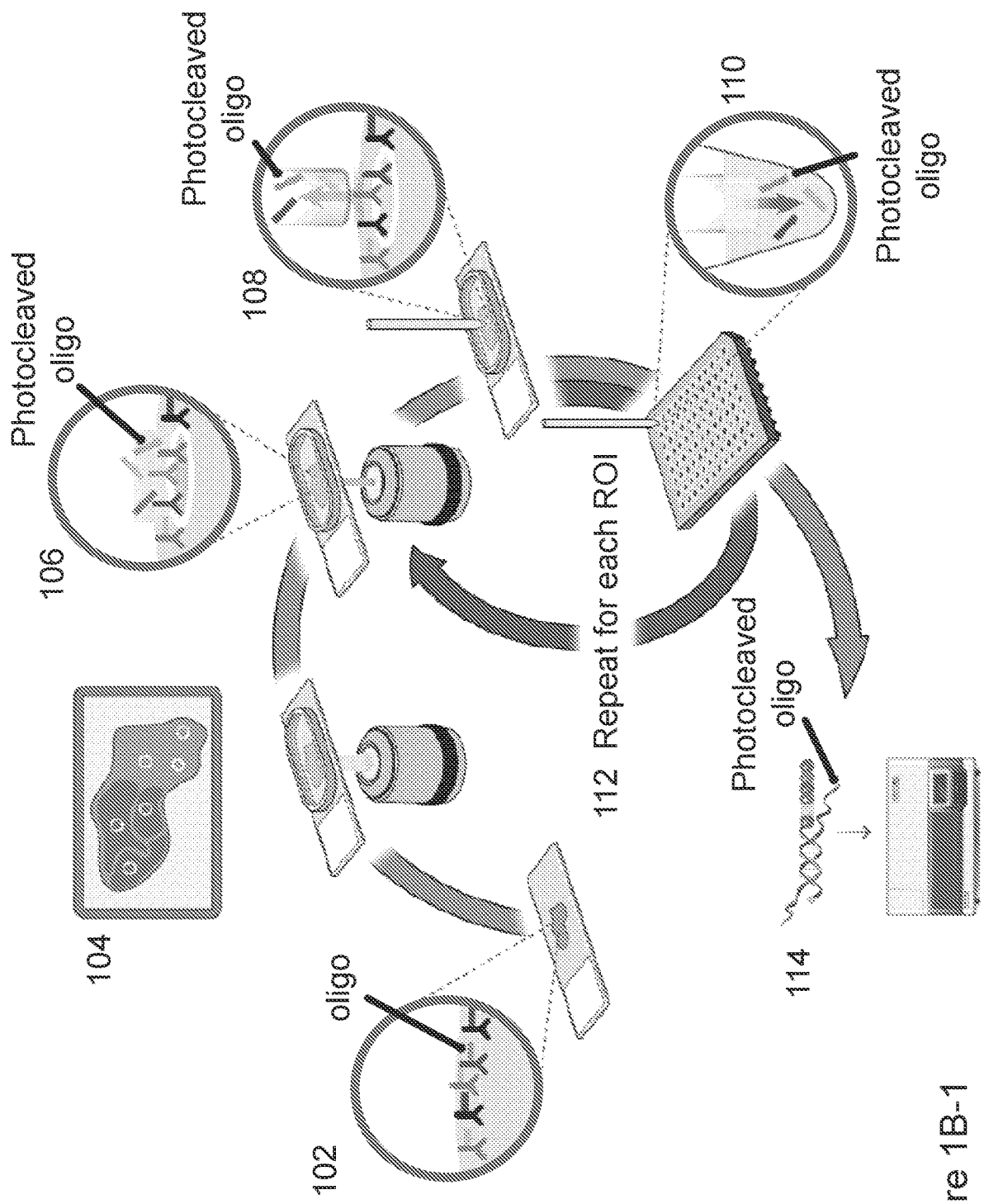
FIG. 1B-1 illustrates a schematic of a process for imaging one or more regions-of-interest (ROIs), using a DSP system, according to some embodiments of the present disclosure.

A high-level overview of steps performed by at least some embodiments of the present disclosure are shown in FIG. 1A (which is a portion of the process outlined in FIG. 1B-1). Specifically, tissue is imaged by the DSP system to find fluorescently tagged antibodies 101, ROIs are determined, illuminated with UV and collect DNA tags via capillary means 103, and then the collected DNA is then hybridized to barcodes in plate and index counts to the specific ROIs 105.

More specifically, according to some embodiments, and as shown in FIG. 1B-1, the process begins by staining a slide with tissue thereon having oligo-conjugated antibodies 102, the slide is then imaged with the DSP system (according to some embodiments), and one or more ROIs are selected 104. The one or more ROIs are then exposed to UV light 106, so as to cleave off oligonucleotides ("oligos") off antibodies in the one or more ROIs. From there, the cleaved off oligos are aspirated 108 from the slide, via, for example, a microcapillary device. The collected oligos may then be placed into an assay 110 (e.g., 96-well plate). This process is repeated 112 for each ROI selected. After the oligos are dispensed into the assay, the oligos are hybridized to barcodes, and then quantified 114 via a quantification system (e.g., NanoString nCounter® platform system).

Figures 1, 1B, 2:
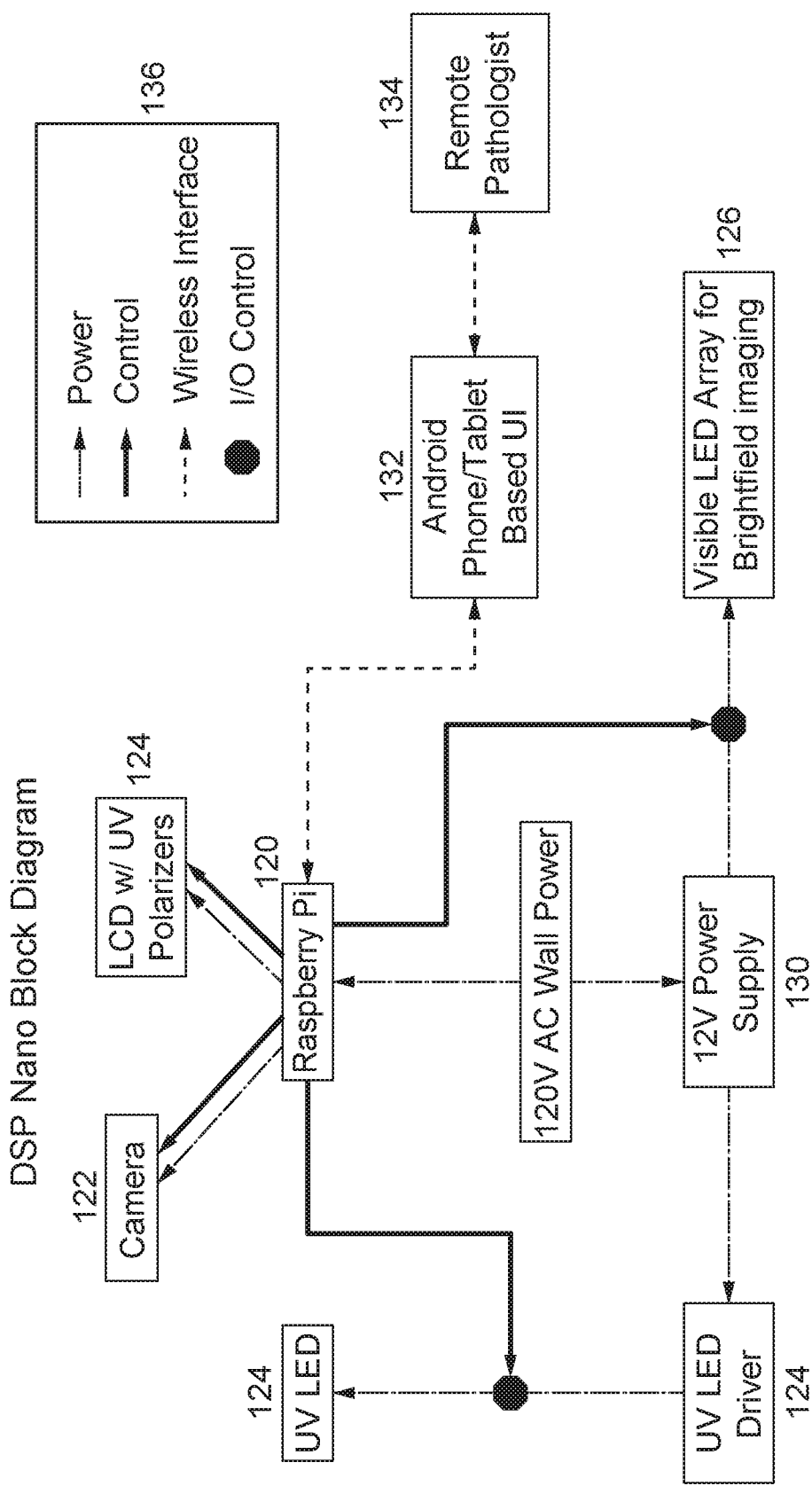

FIG. 1B-2 illustrates an exemplary block diagram of a DSP system according to some embodiments. As shown, a processor (e.g., "Raspberry Pi", "Arduino Uno", and the like) 120 is in communication (e.g., digital) with a camera 122, an LCD 124 with UV polarizers (for example), UV LED 124a and/or UV LED diver 124b, and a visible LED array 126 (for example), used for bright field imaging. Supplied power can be either AC or DC, which supplies, for example an appropriate amount of power to power the system (e.g., 25 watts or less), for powering, for example, the photomasking means, the UV and visible light sources, as well as any processor and communication means that may be provided. Thus, components (e.g., processor, UV LED, UV LED driver, visible LED array, etc.) can be configured to receive power from a typical, standard AC power supply 128 (e.g., wall outlet or dedicated power supply), and/or a dc power source (e.g., 12V power supply 130). The processor can include or have access to computer instructions operable on the processor to cause the processor to control one or more of such components, and can also include instructions (and associated hardware, if needed, e.g., wifi, Bluetooth, cellular, wired) to communicate information obtained or needed to/from a mobile device 132 or other remote computing device/system (e.g., desktop, laptop, server). The remote device can be accessible by a pathologist 134 to review results and/or directed processes carried out by the system (according to some embodiments). FIG. 1B-2 also includes a legend 136 regarding the different processes being illustrated according to some embodiments (e.g., power, control, interfacing, and input/output). Again, the processor can be configured to provide graphics support enabling the creation of photomasks with adjustable aperture sizes and location, as well as a calibration grid as illustrated in FIG. 4D (e.g., for a personal mobile device application), including, for example, four-white dots 480 or corners 482 on a black or dark colored background, a cyan rectangle 484 on a white or light background, or single pixel illumination 486 on black or dark background. In some embodiments, upon startup, the processor can be configured to cause a calibration grid to be displayed onto the LCD, and wait for coordinates to be sent to a processor in the DSP (e.g., pairing via Bluetooth). Once received, an appropriate photomask is displayed on the LCD to highlight a user selected ROI, the backlight is turned off, and the UV source is turned on for a predetermined period of time such as, for example, three minutes, two minutes, one minute or 30 seconds).

Figure 1D:
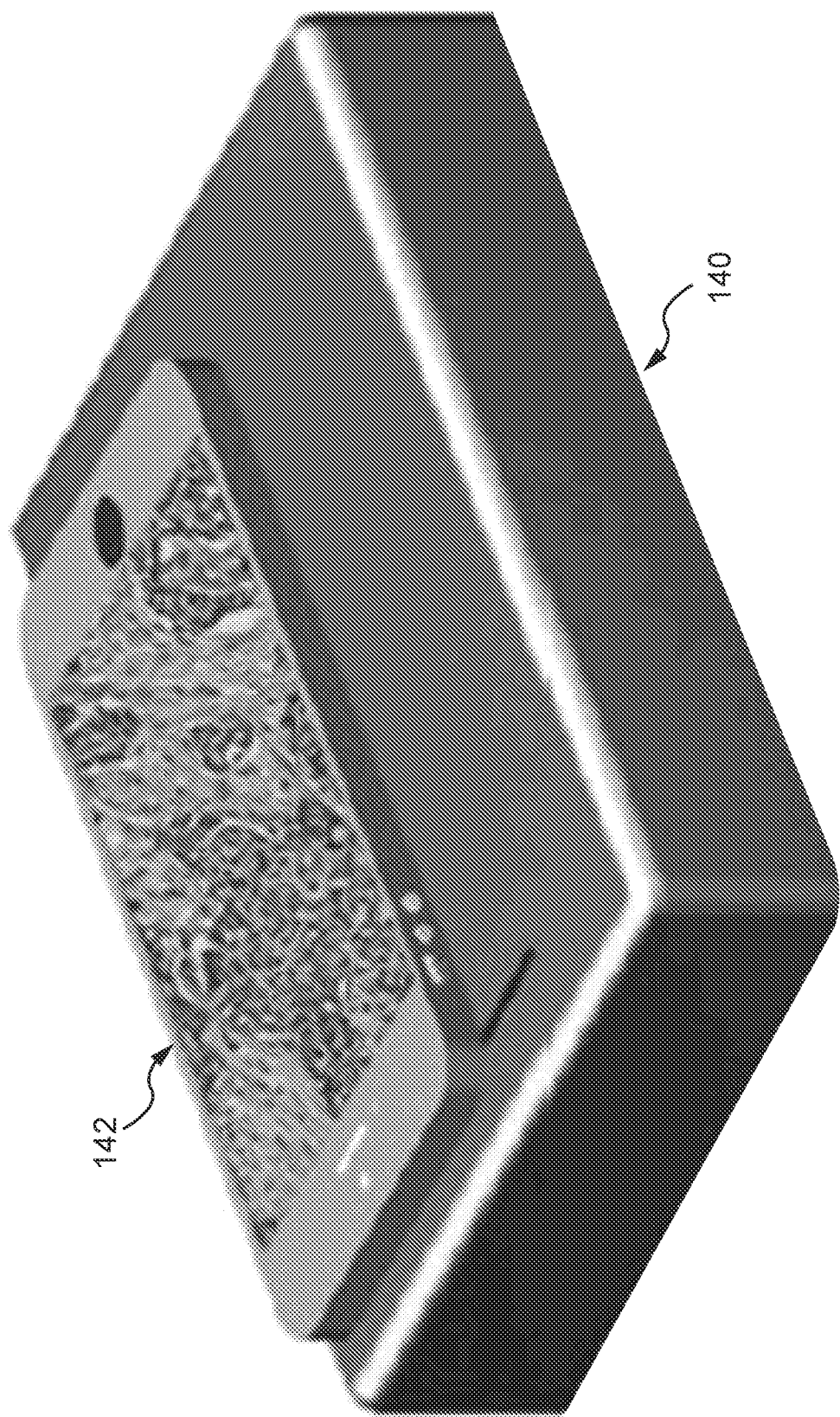
FIG. 1D is a perspective view of some components of a DSP system according some embodiments of the present disclosure.

Accordingly, in some embodiments, an example of which is shown in FIG. 1D, a digital spatial profiling (DSP) system 140 is provided and comprises, at least one of, and in some embodiments, a plurality of, and in still further embodiments, all of, a housing, and a power source, a processor, a UV source (UVS), e.g., a UV LED(s), a visible light source (VLS) for bright field imaging (e.g., LCD backlight), photomasking means (e.g., LCD) configured to selectively illuminate a tissue sample with UV light from the UV source and/or visible light from the visible light source, as well as a chamber (not shown) within the DSP system (e.g., a chamber within a housing) configured to receive at least a portion of the slide having the tissue thereon, via, e.g., a slot, (not shown). A mobile device 142 is also part of the system (according to some embodiments).

Figures 1, 2C:
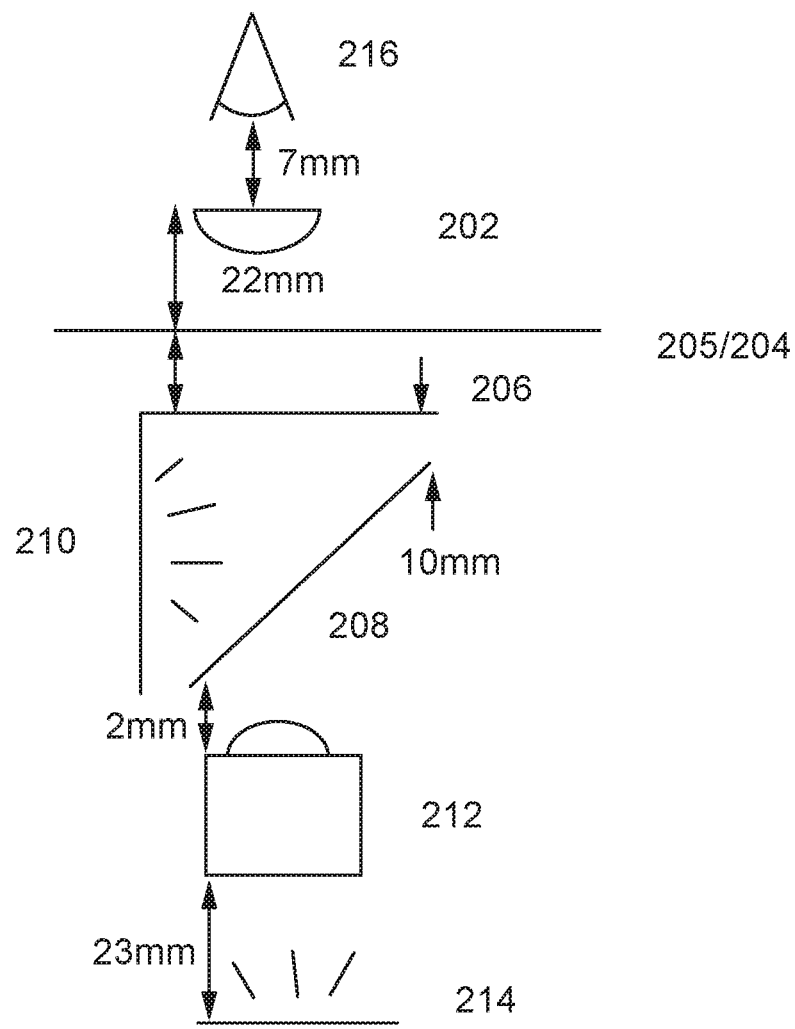

FIG. 2A is a schematic of at least a portion of a DSP system according to some embodiments of the present disclosure. As shown, system 200 includes an objective lens 202, an LCD 206, a dichroic mirror 208, an LCD backlight 210, a UV LED 214, and a condenser lens 212. A glass slide 204 containing a tissue sample 205 is placed in a portion of the system arranged for imaging and exposure to light, UV or otherwise. In the illustrated example, the slide is placed adjacent or near to the LCD photomasking means. The imager, i.e., a mobile device including a camera 216, is arranged within the system so as to image the tissue on the slide. FIG. 2C-1 is similar to FIG. 2A, but includes an example of the distances certain components are placed among other components of the system, according to some embodiments. Accordingly, in some embodiments, the photomasking means is preferably arranged at a predetermined distance from the tissue, the distance of which can be configured such that the tissue is not obscured by the pixel grid. The predetermined distance can be between approximately 0.01 to 5 mm, between approximately 0.50 to 2.5 mm, between approximately 0.75 to 2.25 mm, or between approximately 1 to 2 mm. Additionally, the predetermined distance can be configured to at least one of provide clear visualize of tissue, and to minimize diffusion of UV light. In some embodiments, the photomasking means is configured to provide, for example, an illumination resolution of between approximately 50 and 300 nm, a field of view between approximately 1-5 $cm^2$, and/or a magnification of between approximately 1-3×.

FIG. 2B illustrates a schematic of an exploded view of the LCD photomask/functionality 219, with voltage "on" 221, and voltage "off" 223. Accordingly, in some embodiments, the LCD 219 includes, a polarizing filter 220, a transparent electrode 222, a liquid crystal 224, a second transparent electrode 226, a second polarizing filter 228, and a screen 230. When the voltage is on 221, the screen is dark and initially received un-polarized light (visible and/or UV) is blocked from passing through the LCD. When the voltage is off 223, received un-polarized light is allowed to pass through to the screen. Thus, illustrating the structure of the LCD and how it performs as a photomask via the "ON-OFF" of one or more pixels, to pass and block light.

Figures 2, 2C, 3:
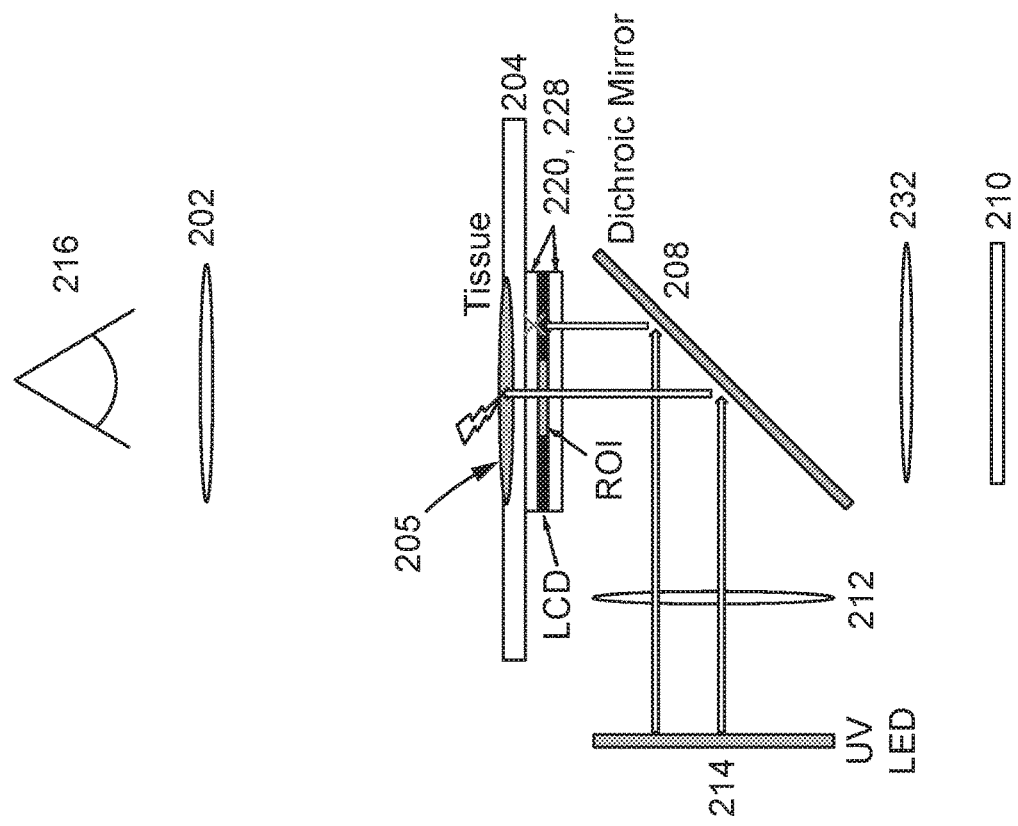
Figures 2, 2C:
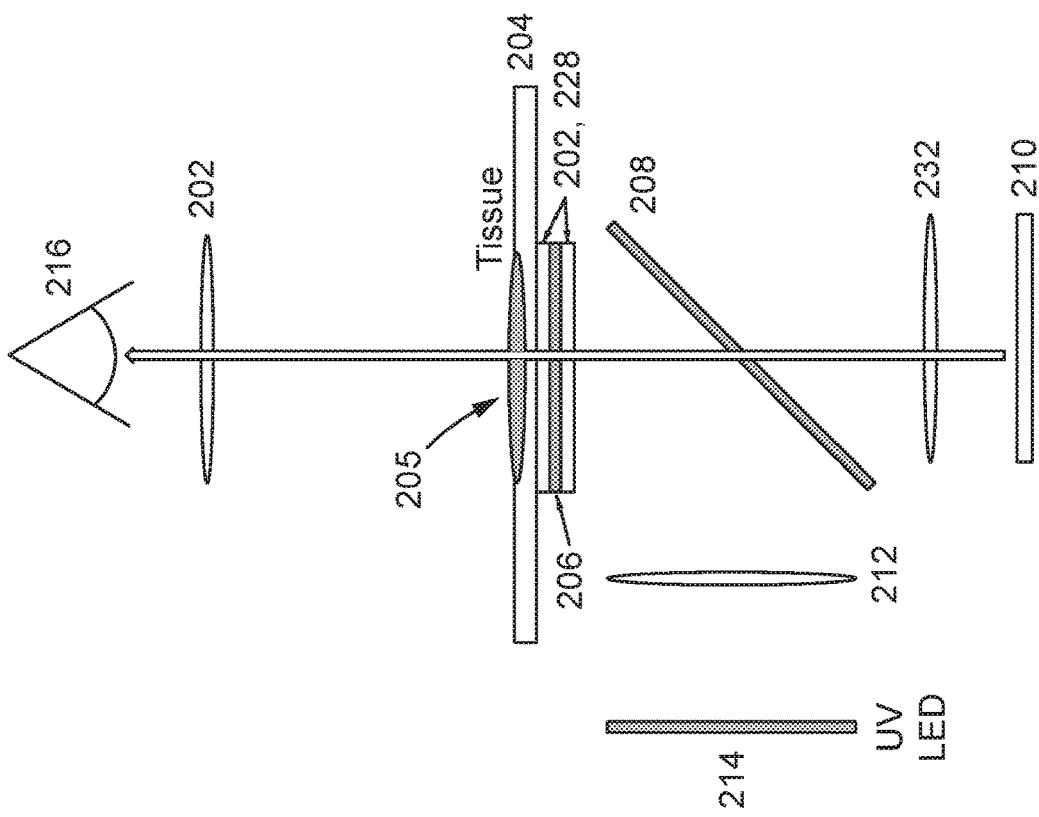
Figure 2D:
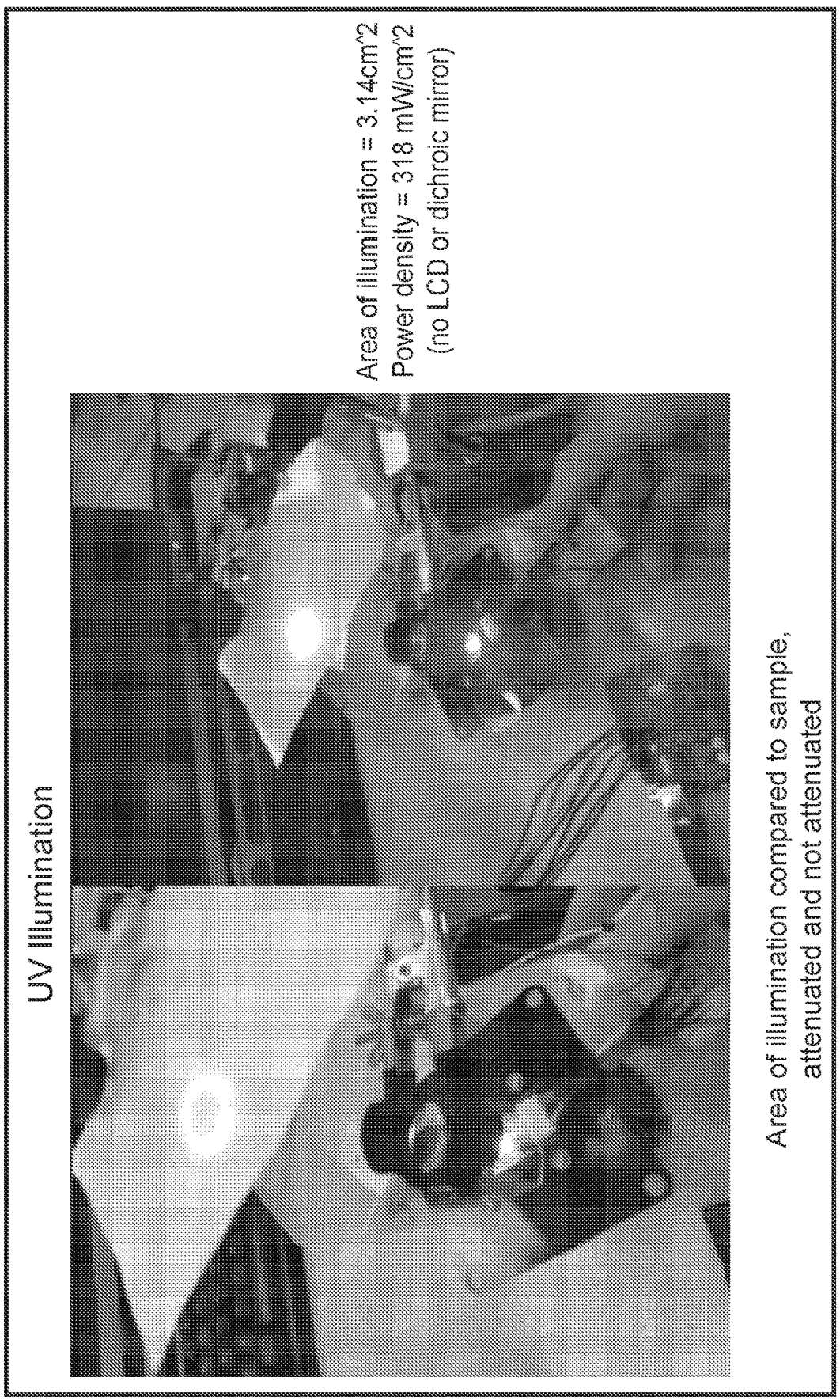
FIG. 2D illustrates an attenuation of UV illumination by a UV LED component of a DSP system according to some embodiments of the present disclosure.

Similar to FIG. 2A, FIGS. 2C-2 and 2C-3 illustrate operation of the DSP system, according to some embodiments, illustrating how the LCD 206 and accompanying polarizing filters 220, 228 enable only one or more selected ROIs to be exposed to UV by action of LCD masking. In FIG. 2C-2, the system is shown prior to exposing any of the tissue (ROI or otherwise) to UV light, an allowing the tissue to be illuminated by white LED light (thus, allowing a user to select one or more ROIs), and FIG. 2C-3, illustrates exposure of selected ROIs, to UV light by action of the LCD mask. Specifically, it can be seen that the LCD 206 can block passage of UV to all but ROIs of the tissue sample. It is worth noting that in some embodiments, a diffuser 232 can be included to diffuse the white LED light. In some embodiments, UV light can be attenuated (see, e.g., FIG. 2D), using, for example the photomasking means for example (in some embodiments).

Figures 1, 2E:
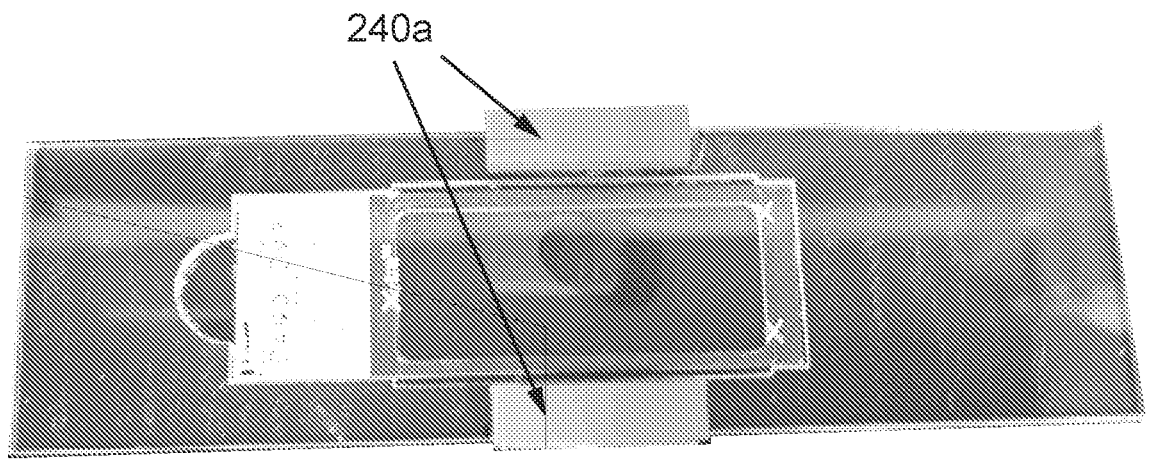
Figures 2, 2E:
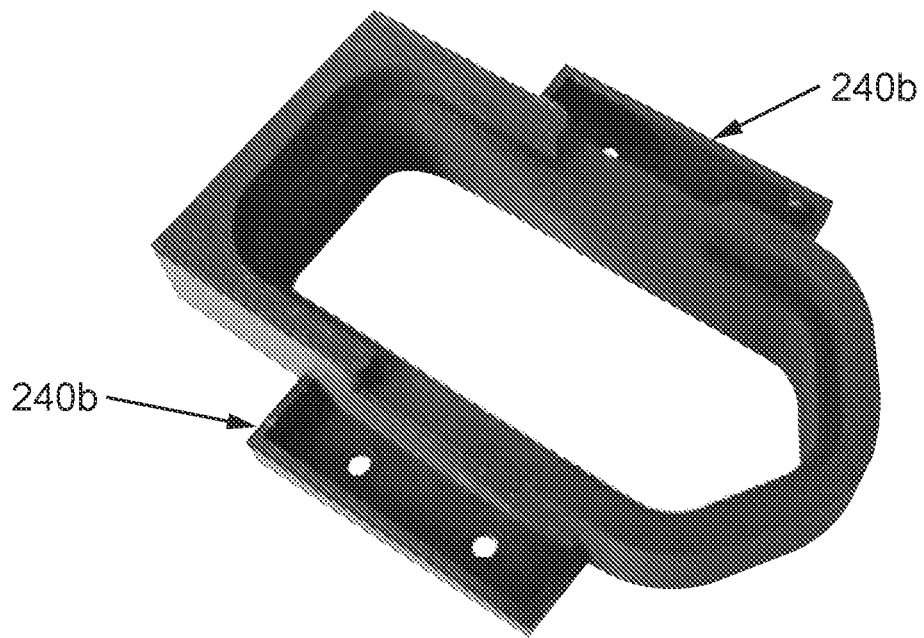
Figures 2, 2E, 3:
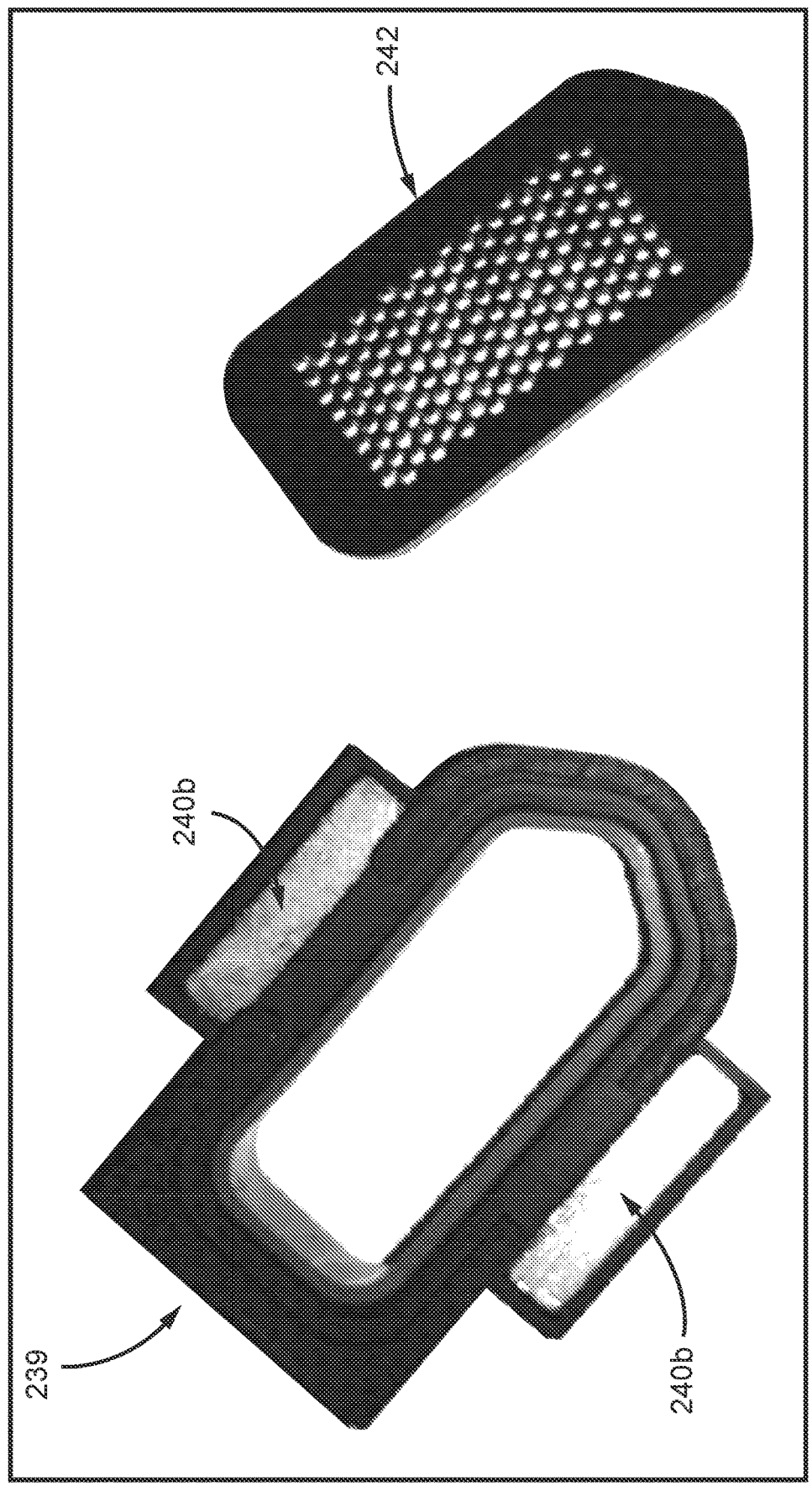

A slide can be received into the chamber (and/or housing) of the DSP system according to some embodiments, via a "box" configuration, such that a top or side of the box opens (via, e.g., hinges). The slide can be movable relative to the chamber (or housing containing the chamber, optics, and/or UV/light sources), where the chamber can be configured with a liquid environment for tissue, and sealed from liquid escaping, by any sealing means known in the art; e.g., gasket, see FIGS. 2E-1 through FIG. 2E-5, which illustrate a slide (FIG. 2E-1, and gasket configurations which may be used therewith; FIGS. 2E-2 and 2E-3). Such slide and gasket configurations can utilize magnetic means 240A on the slide, for example, and 240B on the gasket 239 (within a housing and/or frame), where, e.g., the magnetic means may be permanent and electromagnetic on one and/or another of the slide and gasket/housing/frame, for mated attachment between the slide and the gasket. The slide and gasket configurations can include a guide means such as a grid barrier 242 (can also be referred to as a guide, in some embodiments), as illustrated in FIG. 2E-3, which can be configured within or proximate to a slide and gasket configuration to allow for guided pipetting of cleaved oligos manually or via machine/robotically. FIGS. 2E-4 and 2E-5 illustrate use of a grid 242 of capillary tubes 243 configured to collect fluid through capillary action (as well as dispense fluid). As shown, the grid can be configured to fit within components of the system, e.g., gasket 239. As shown, the grid 243 and tubes 243 can be inserted into the gasket 239.

Figure 3A:
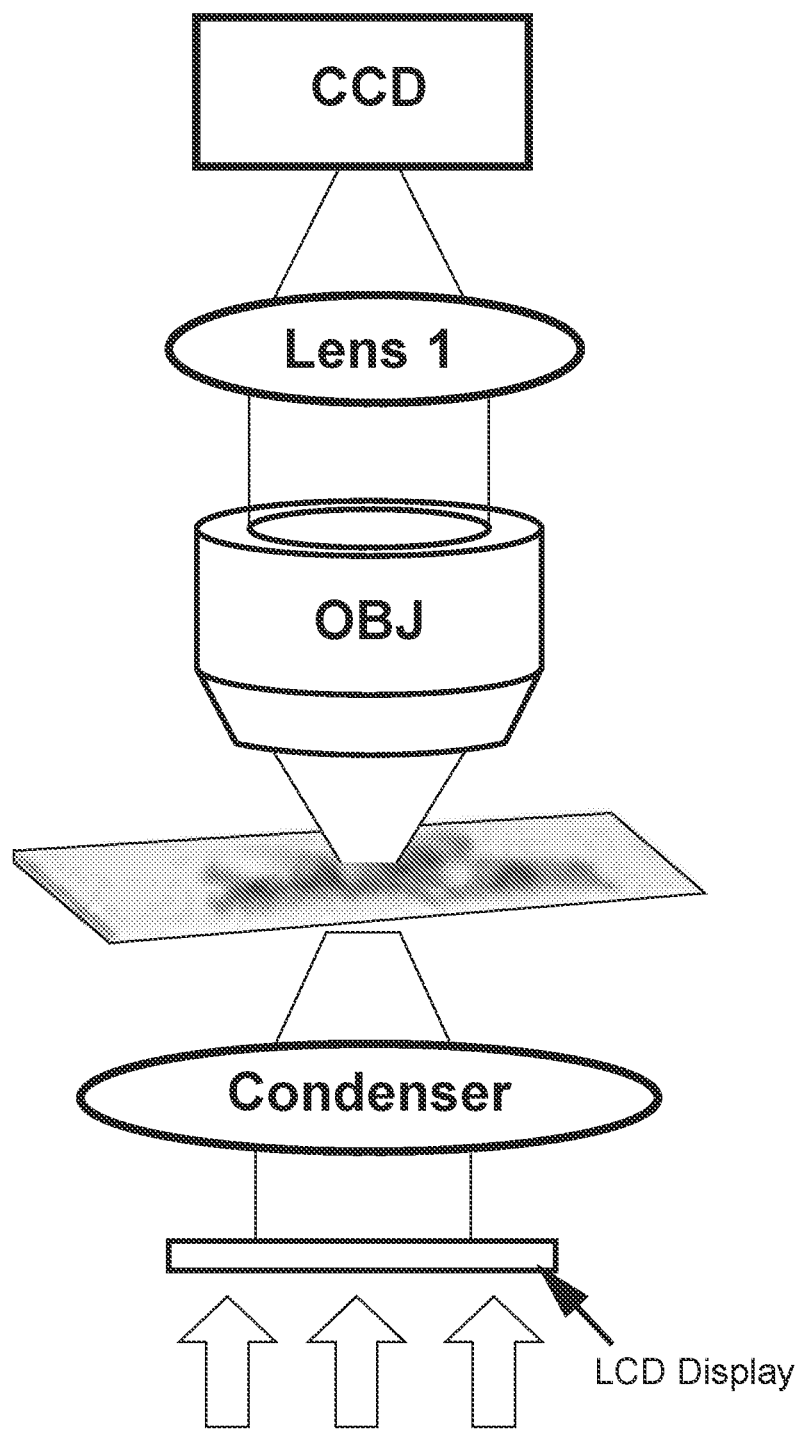
FIG. 3A illustrates a schematic of a DSP system according to some embodiments of the present disclosure, which is similar to that which is illustrated in FIG. 2A.
Figure 3B:
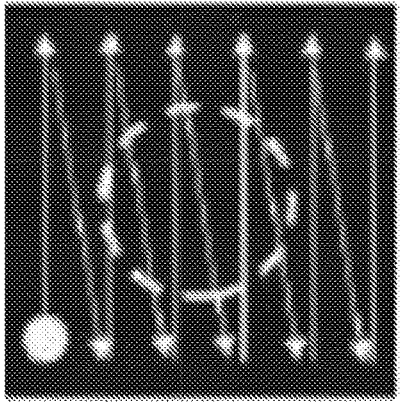
FIG. 3B illustrates exemplary display patterns for achieving different microscopy modalities, according to some embodiments of the present disclosure.
Figure 3B:
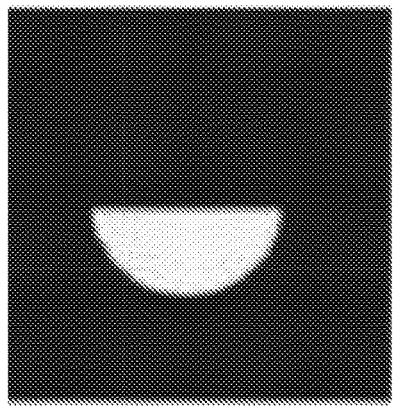
Figure 3B:
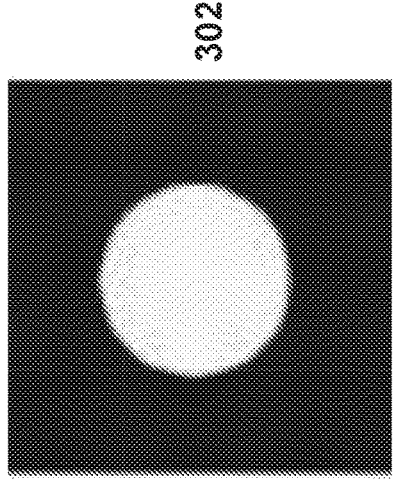
Figure 3B:
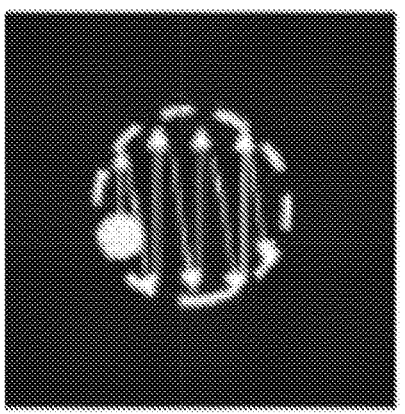
Figure 3B:
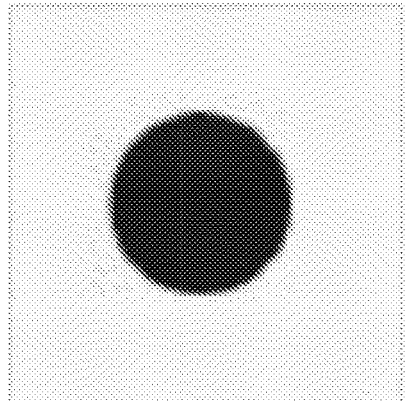

The system may also include optic means (e.g., lenses and like, including an objective lens) configured to at least one of direct and/or focus the UVS and/or VLS onto at least one of the tissue, the chamber, the photomasking means, and a camera sensor (e.g., "phone camera") operably linked to a personal mobile computing device (PMD). At least one of the housing and chamber is configured for removable attachment to the PMD such that the camera sensor can image the tissue. FIG. 3A illustrates a high-level overview of the system according to some embodiments (similar to FIG. 2A). FIG. 3B illustrates different patterns which can be displayed for achieving different microscopy modalities for the DSP system according to some embodiments, including bright-field 302, dark-field 304, phase-gradient 306A, 306B, 3D 308 and super-resolution 310.

The optic means, according to some embodiments, may include the UV source and VLS (though, in some embodiments, such structure can be also considered separate from the optic means), one or more of any of: condenser lenses, scan lenses, dichroic mirrors, photomasking means (see below, and elsewhere herein), objective lenses, cameras (e.g., a personal mobile device with camera, and the like). The optic mean, in some embodiments, is configured to illuminate a tissue sample with UV light from the UV source, visible light from VLS, or visible or white light from the LCD backlight. The dichroic mirror is configured to allow the re-direction of light from multiple sources (e.g., two (2) sources), into an optical axis (in some embodiments, a single optical axis), so it reaches the sample only in user-determined locations.

As noted according to some embodiments above, the photomasking means can comprise at least one of: an LCD (which can include a backlight, e.g., as shown in FIG. 2A), an LCD configured as a programmable aperture, so as to structure at least one of UV and visible or white light to reach the tissue only in a regions-of-interest (ROI), a digital micro-mirror device (DMD), a liquid crystal on silicon (LCoS) display, an organic light-emitting diode (OLED), a micro light-emitting diode (μLED) array, a fiber optic bundle, a liquid crystal displays (LCD), a scanning laser, and, a physical barrier. In some embodiments, where the photomasking means comprises an LCD, the LCD may include a pixel grid.

FIGS. 4A and 4B, which correspond to a DSP system according to some embodiments, similar to that of FIGS. 2A and 2B, but illustrating a digital micro-mirror device (DMD/liquid crystal on silicon (LCoS)), reflective mask structure and operation, corresponding to a form of the photomasking means. A DMD is typically a chip having on its surface a multitude (e.g., several hundred thousand) microscopic mirrors arranged in an array (e.g., rectangular) which correspond to "pixels" used for photomasking. The mirrors can be individually rotated (e.g., ±10-12°), to an on or off state. In the on state, light from a light source is reflected into a lens (making the pixel appear bright), and in the off state, the light is directed elsewhere (e.g., a heatsink), making the pixel appear dark. Accordingly, as shown, a tissue slide 403 with tissue 405 is placed in the system, where it can be illuminated with white light 410, via lens 407 and dichromatic mirror 407. The DMD/LCoS 420 performs masking to direct the UV light 414 onto specific ROIs 403b within the tissue sample 405a on the slide 403. FIGS. 4B-1, and 4B-2, illustrates the functionality of a DMD/LCoS components (e.g., independently movable micro-mirrors 450, secondary mirror 452 and silicon chip 454).

Figure 4C:
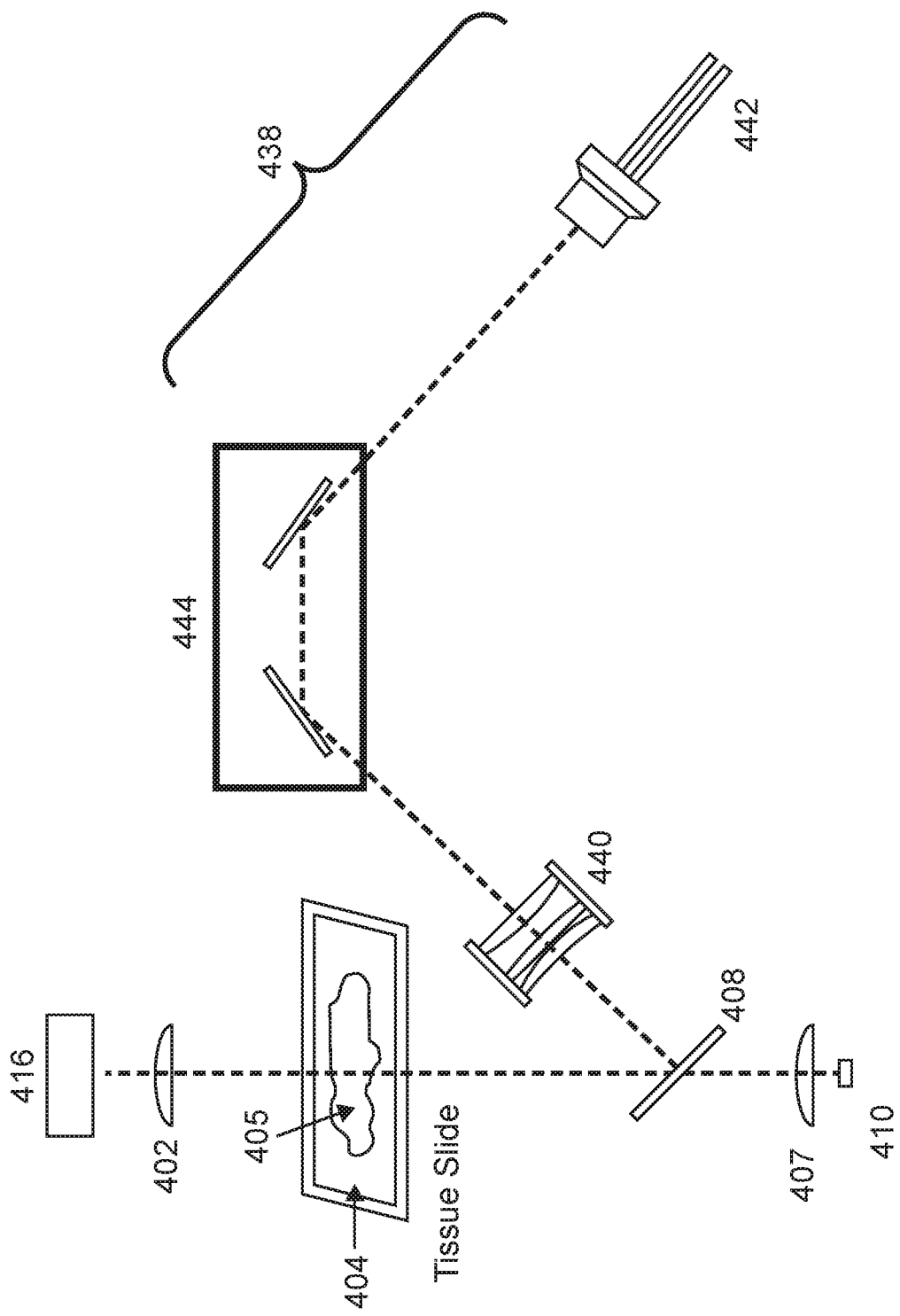
FIG. 4C, is a schematic of a DSP system, according to some embodiments of the present disclosure; illustrating the structure and operation of a scanning laser.
Figure 4D:
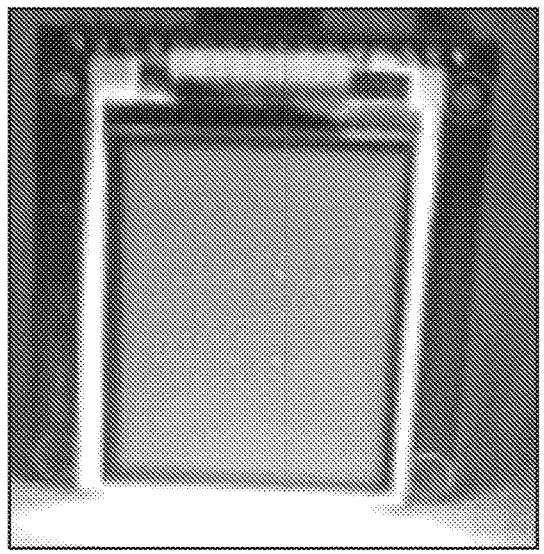
FIG. 4D illustrates calibration schemes for a DSP system according to some embodiments of the present disclosure.
Figure 4D:
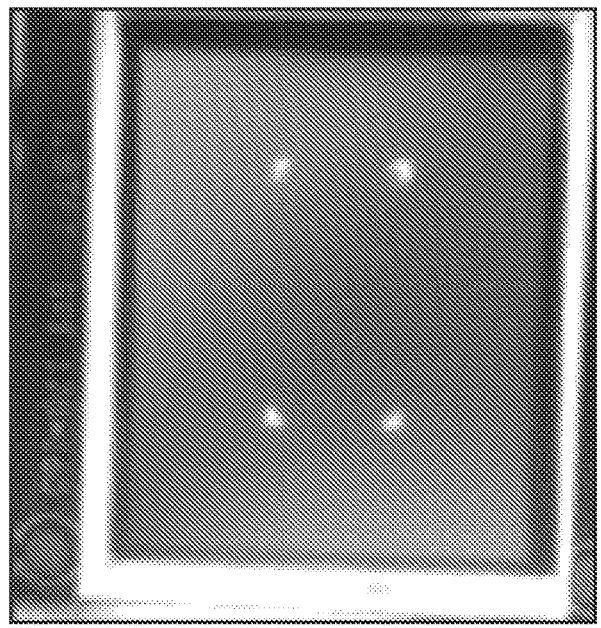
Figure 4D:
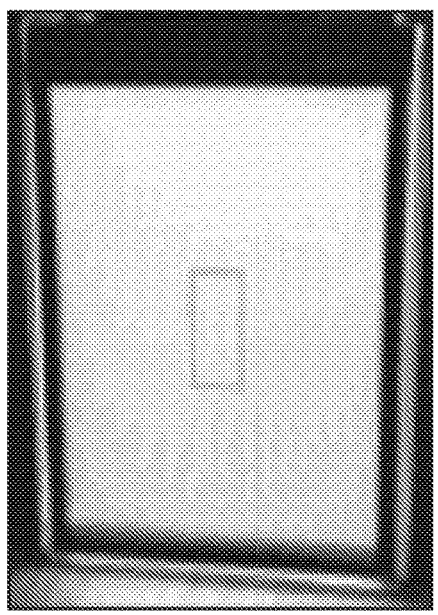
Figure 4D:
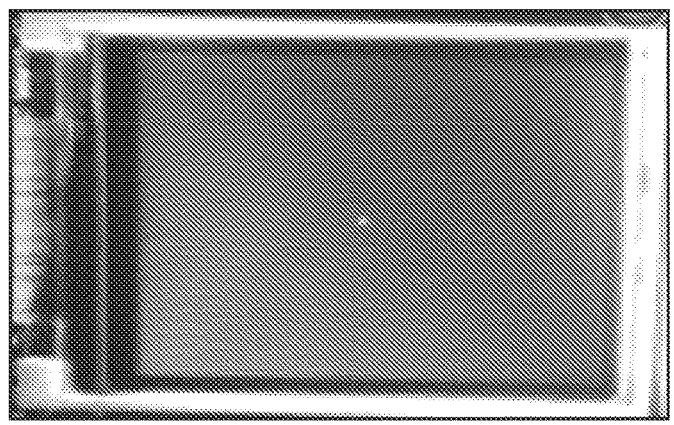

FIG. 4C, which correspond to a DSP system according to some embodiments, are similar to that of FIGS. 4A and 4B, but make use of a scanning laser system 438, corresponding to a yet another form of the photomasking means. The scanning laser typically includes moveable mirrors, such as an XY galvanometer mirror 444 for example, capable of directing a laser beam from laser 442 in at least two dimensions via scan lens 440 (and then via the other noted components of the dichroic mirror 408, camera 416, lens 402, slide 403, tissue 405a, while LED 410 and lens 407). Scanning can be in the form of raster scanning or vector scanning. When scanning, the scanning laser is directed only to that part of the tissue to be illuminated which correspond to "pixels" used for photomasking.

Figure 5A:
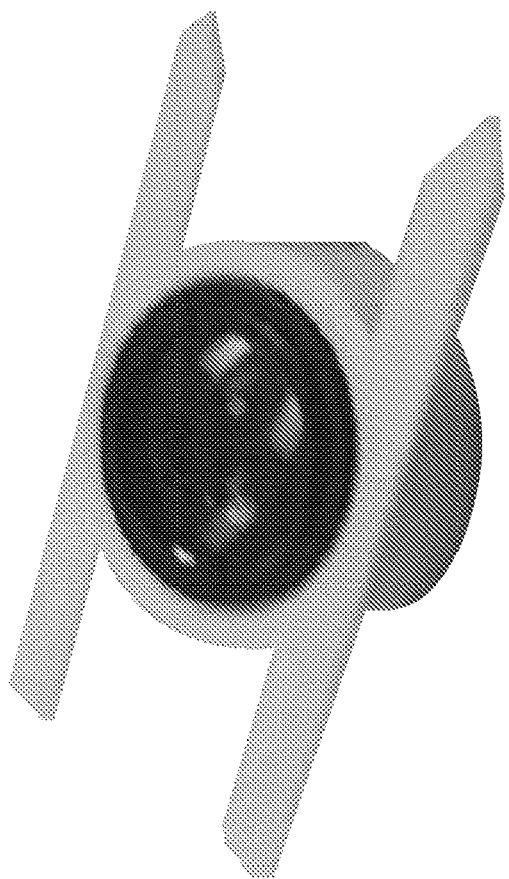
FIGS. 5A-E illustrate exemplary scaffolds and frames for a DSP system according to some embodiments of the present disclosure.
Figure 1:
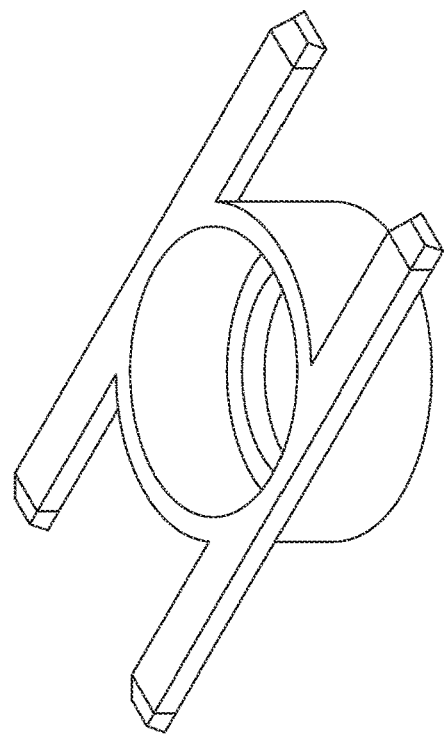
Figures 2, 5B:
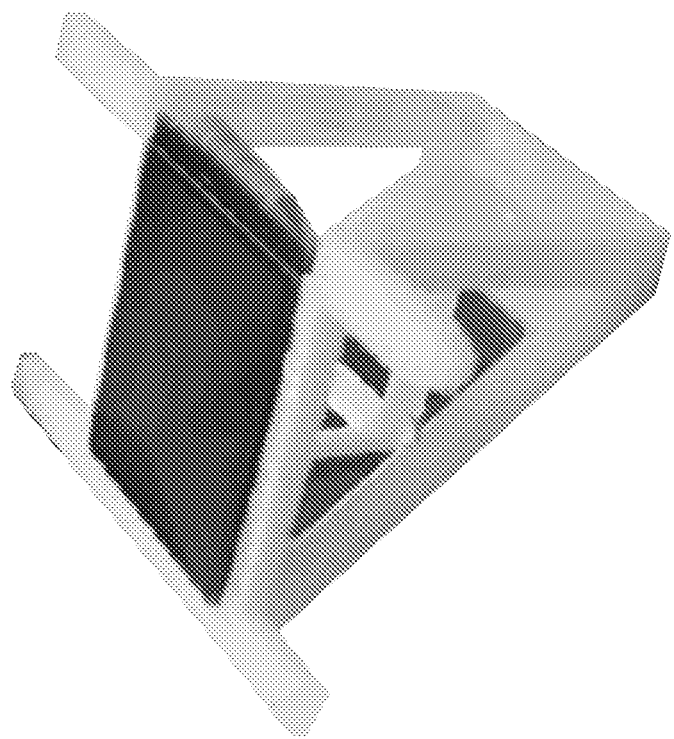
Figures 1, 5B:
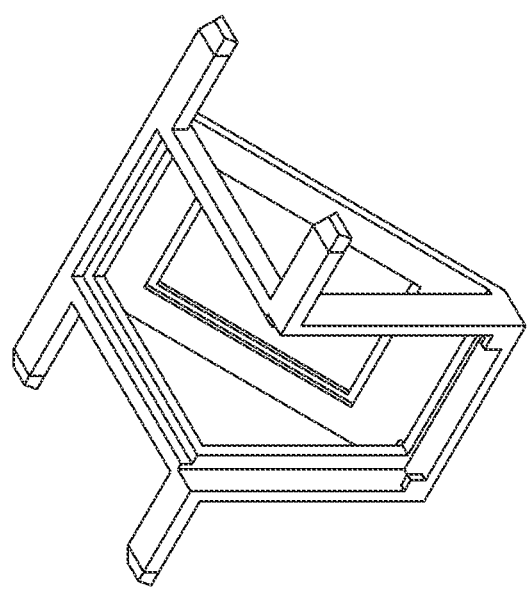
Figures 3B, 5B:
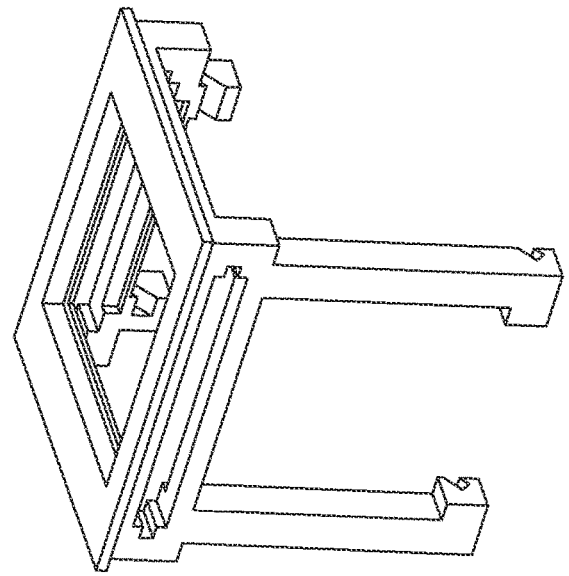
Figures 3A, 5B:
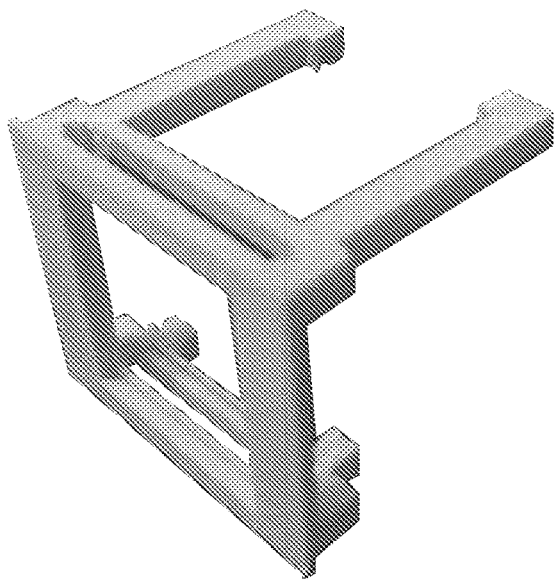
Figures 4, 5B:
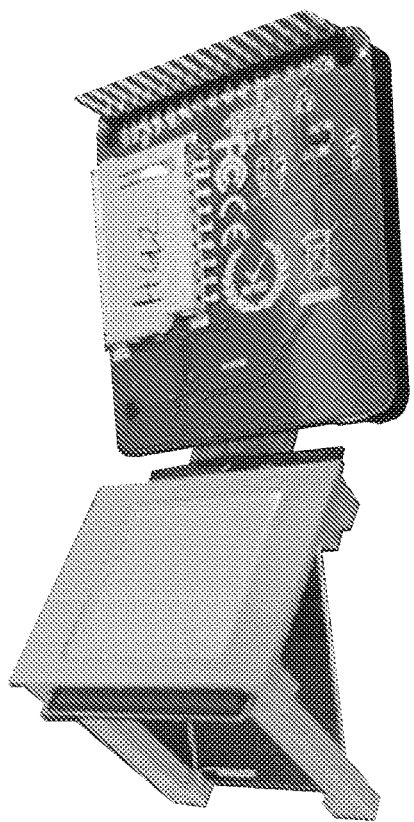
Figure 5C:
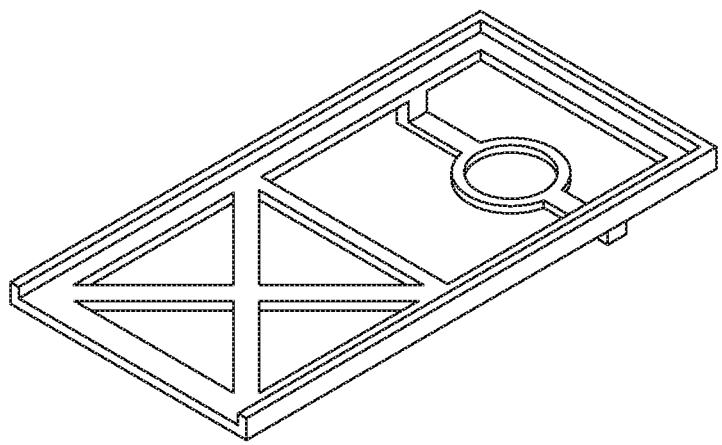
Figure 5D:
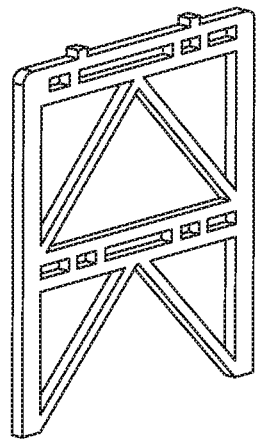
Figure 5E:
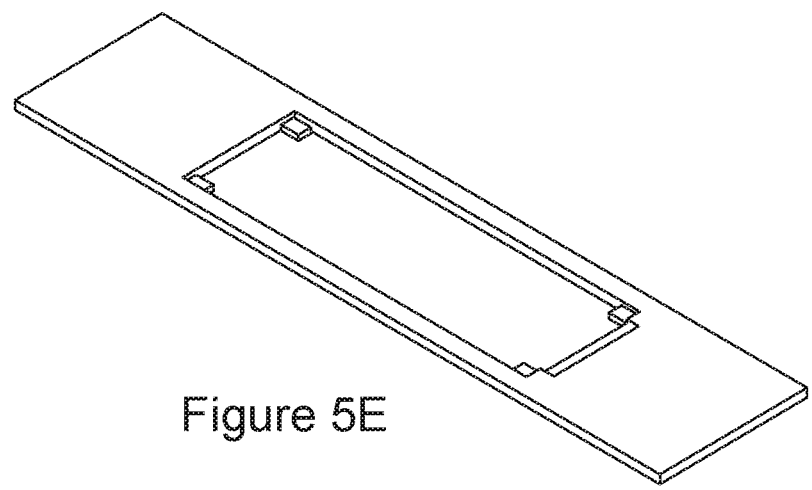
Figure 5F:
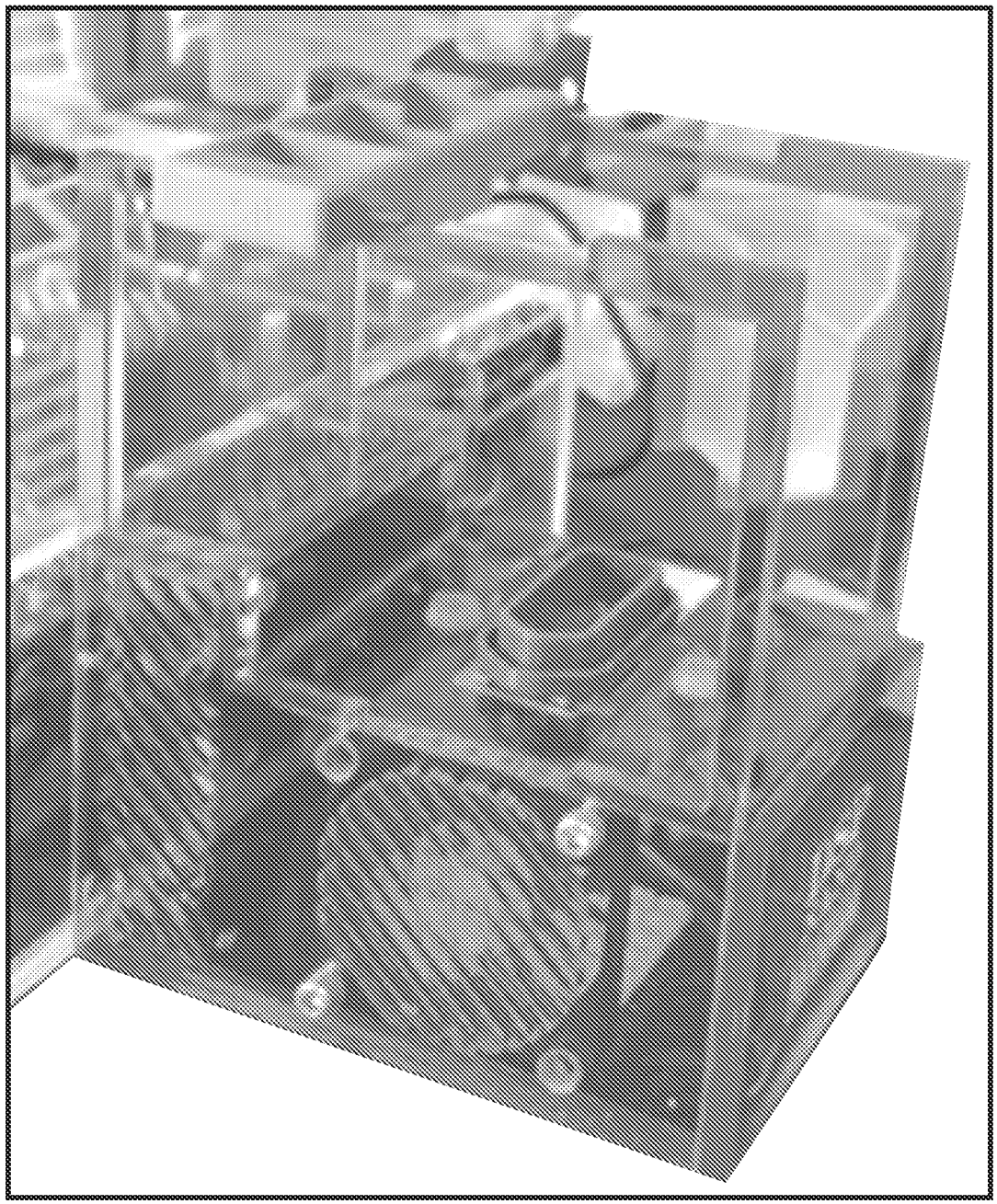
FIG. 5F illustrate an exemplary DSP system housing structure according to some embodiments of the present disclosure.

Housing/frame structure for the DSP, according to some embodiments, can comprise a plurality of components, including, for example, one or more of any of: scaffolds, PMD frames, objective lens frames, slide frames, photomasking frames, condenser frame, and, in some embodiments, at least one thermal management means. FIGS. 5A-E illustrate the various scaffolds and frames for the DSP (e.g., which can form or together be the housing): FIG. 5A-1, 5A-2—condenser frame, for housing the condenser lens; FIGS. 5B-1 and 5B-2—a LCD, dichroic, backlight frame, for holding the photomasking means (e.g., LCD); FIG. 5B-3—a housing/frame for holding the LCD and a lens (e.g., dichroic), FIG. 5B-4—a housing/frame for holding an LCD with a controller, and a lens (e.g., dichroic); FIG. 5C—PMD and/or objective frame, for holding the PMD relative to the housing/chamber; FIG. 5D—a scaffold for various uses (e.g., support for housing/chamber); and FIG. 5E—slide frame, for holding a slide to be received by the chamber, via a slot. The housing can be configured to removably receive a single objective lens frame of a plurality of objective lens frames, where each has a different objective lens and corresponding magnification. Each objective lens frame can be configured so as to provide a different spacing from the camera sensor, and can easily be swapped out for another. Such examples of frames, supports, scaffolds, and the like. FIG. 5F is a perspective view of an assembled DSP system using various frames and scaffolds.

Figure 6:
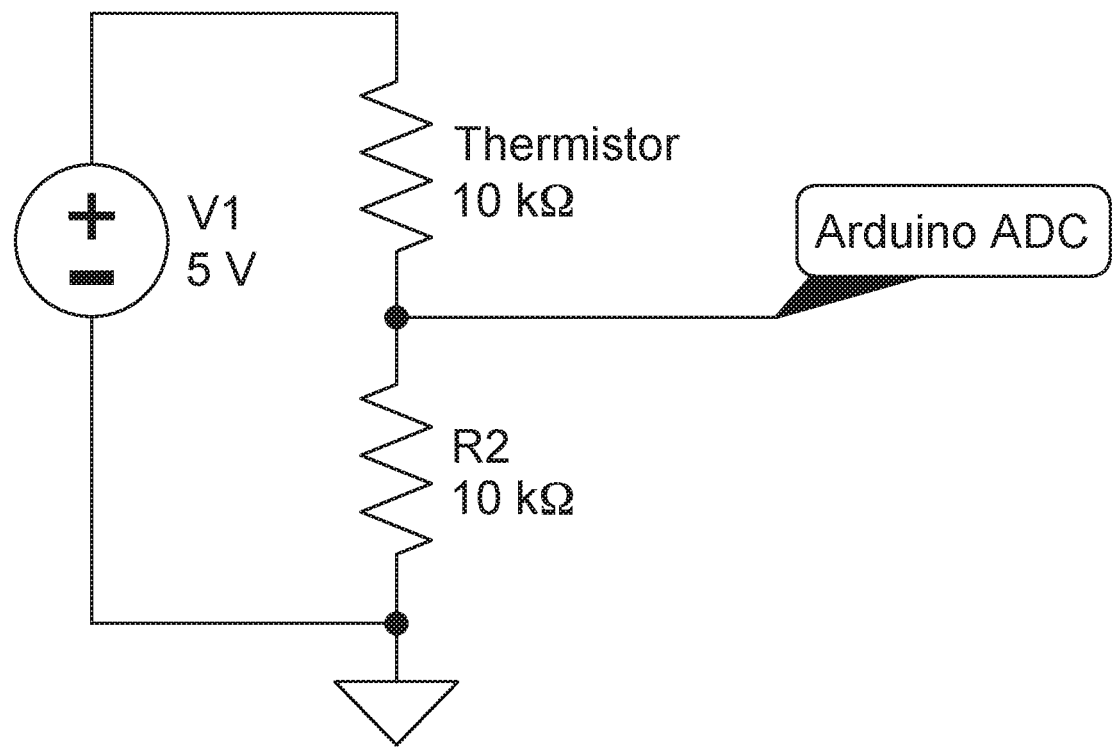
FIG. 6 illustrates an exemplary circuit for thermal management of a DSP system, according to some embodiments of the present disclosure.

A thermal management means can be included in some embodiments of the DSP system, which can comprise at least one of a heat sink, a heat pump, a fan, a liquid cooling system, and a Peltier device. FIG. 6 illustrates an exemplary circuit for thermal management of the DSP, according to some embodiments, which can be operably connected to the processor, via an analog-to-digital convert (e.g., Arduino ADC). The thermal management means can also comprise a plurality of heatsink clips.

Figure 7A:
FIGS. 7A through 7D-7 illustrate screenshots of the graphical user interface (GUI) for a DSP/PMD system/device, according to some embodiments of the present disclosure.
Figure 7B:
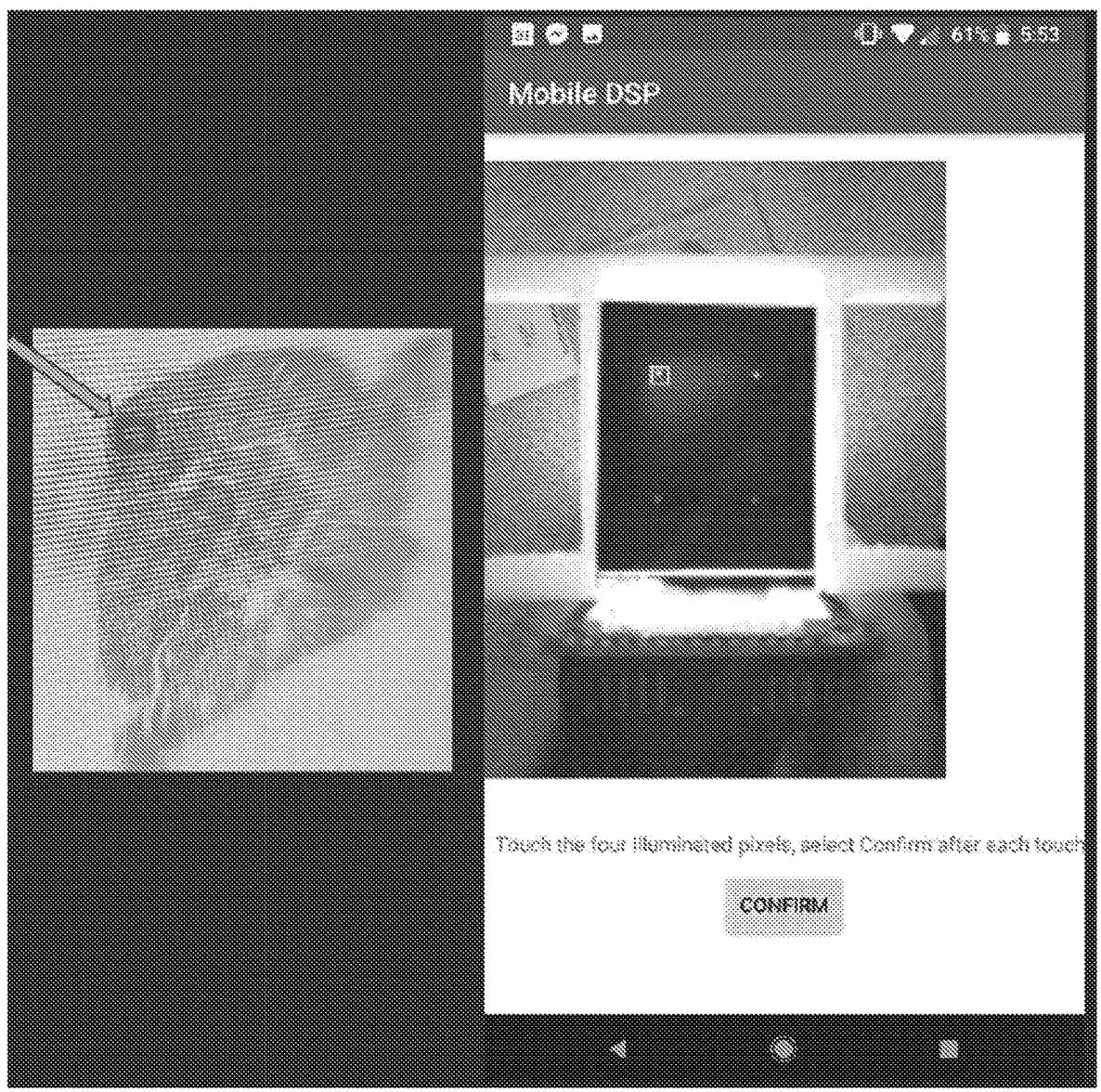

In some embodiments, a software application (e.g., mobile application) is included, which can be configured to operate on a/the processor, which can be configured to cause the PMD to display a graphical-user-interface (GUI), the GUI can be configured to receive user input to select a/the region-of-interest (ROI) of a tissue image obtained via the camera sensor of the tissue slide and presented on a/the display of the PMD. FIGS. 7A-B illustrate example screenshots of the GUI according to some embodiments. The mobile application, in some embodiments, is configured to provide, for example, functional calibration of the LCD. For example, a plurality (e.g., 4 corners of square/rectangle) of pixels of illumination shown on the LCD can be selected by a user (using, e.g., the GUI), to establish a ROI as a position within the four corners (ratio of x and y); see e.g., left hand images on FIGS. 7A-B (see, e.g., also FIG. 4D for calibration schemes of LCD). The application can also display the selected ROI, including recording the location on the image, and the ROI may also be changed, re-selected immediately in case of mistakes, or increased or decreased in size.

Figure 7C:
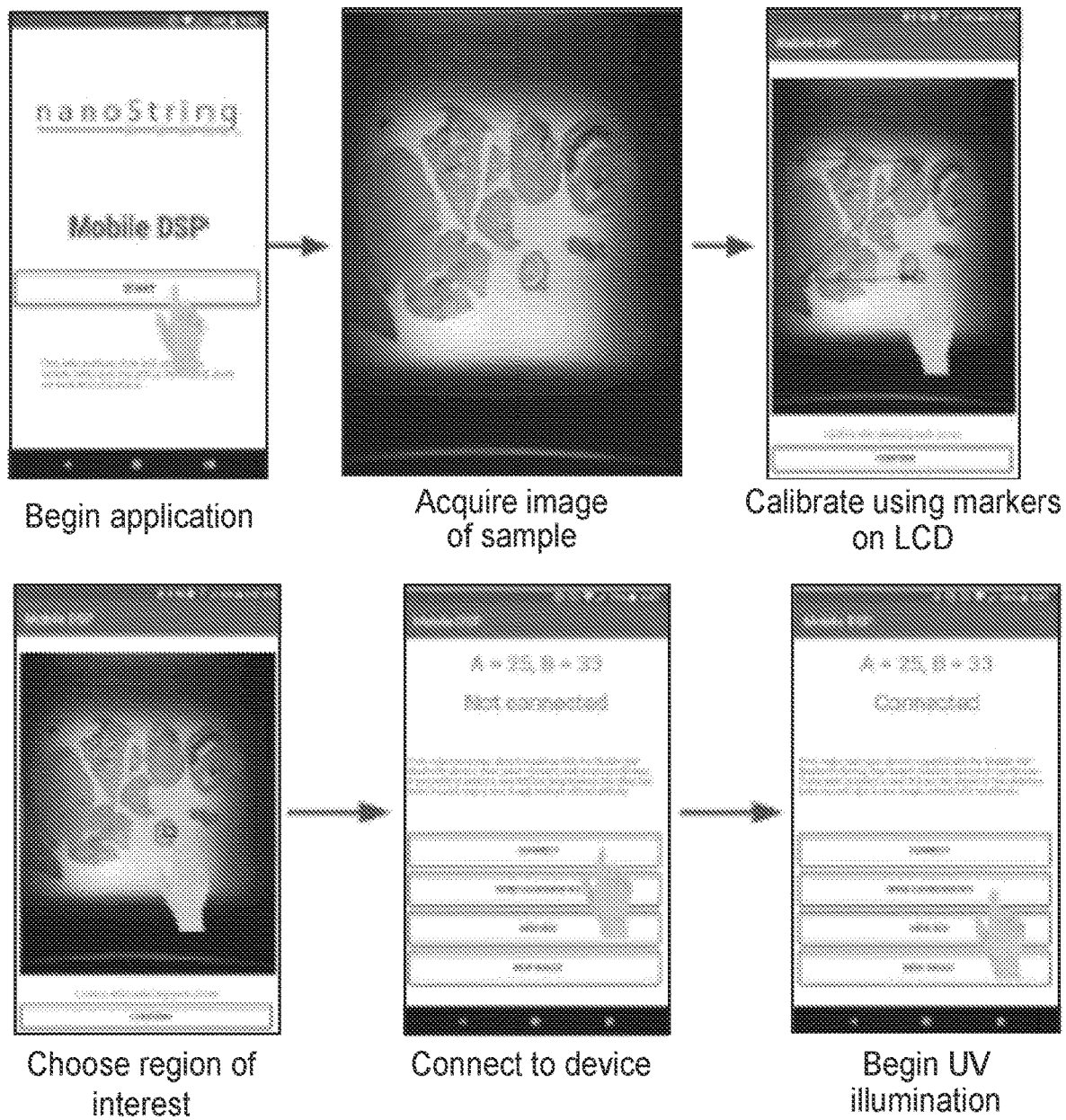

FIG. 7C illustrates example screenshots of an exemplary software application according to some embodiments. Beginning at the uppermost left-hand side of the figure, and proceeding left to right, then down, left to right, the GUI of the mobile application allows the process for imaging the tissue (after the slide having the tissue thereon is received in the chamber), by pressing (via touchscreen), and selecting the region of interests, the "start" button. Thereafter, the tissue is imaged, the likes of which includes controlling the VLS to provide visible light to the tissue sample during image capture. Thereafter, the image is calibrated using at least one (and preferably a plurality) marker on the LCD for example (i.e., the photomasking means).

Next, for example, a ROI is selected by the user via the touchscreen, and the PMD operating the application is paired/connected to the DSP (e.g., Bluetooth). Thereafter, the coordinates of the ROI(s) are sent to the DSP, and UV illumination is begun, to cleave off the oligos bound to antibodies via a photocleavable linker.

Figures 2, 2E, 3, 4:
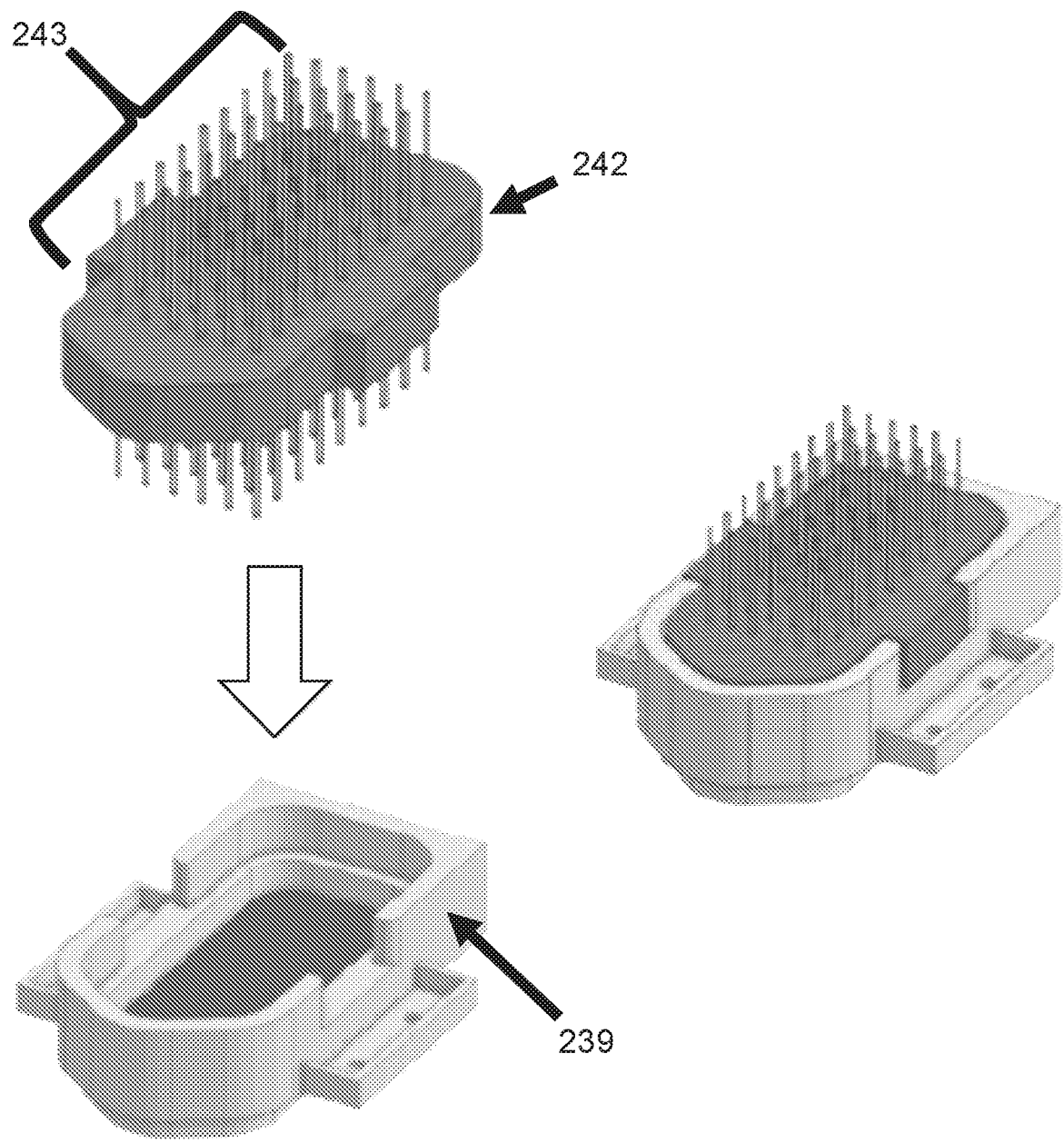
Figures 2, 2E, 3, 4, 5:
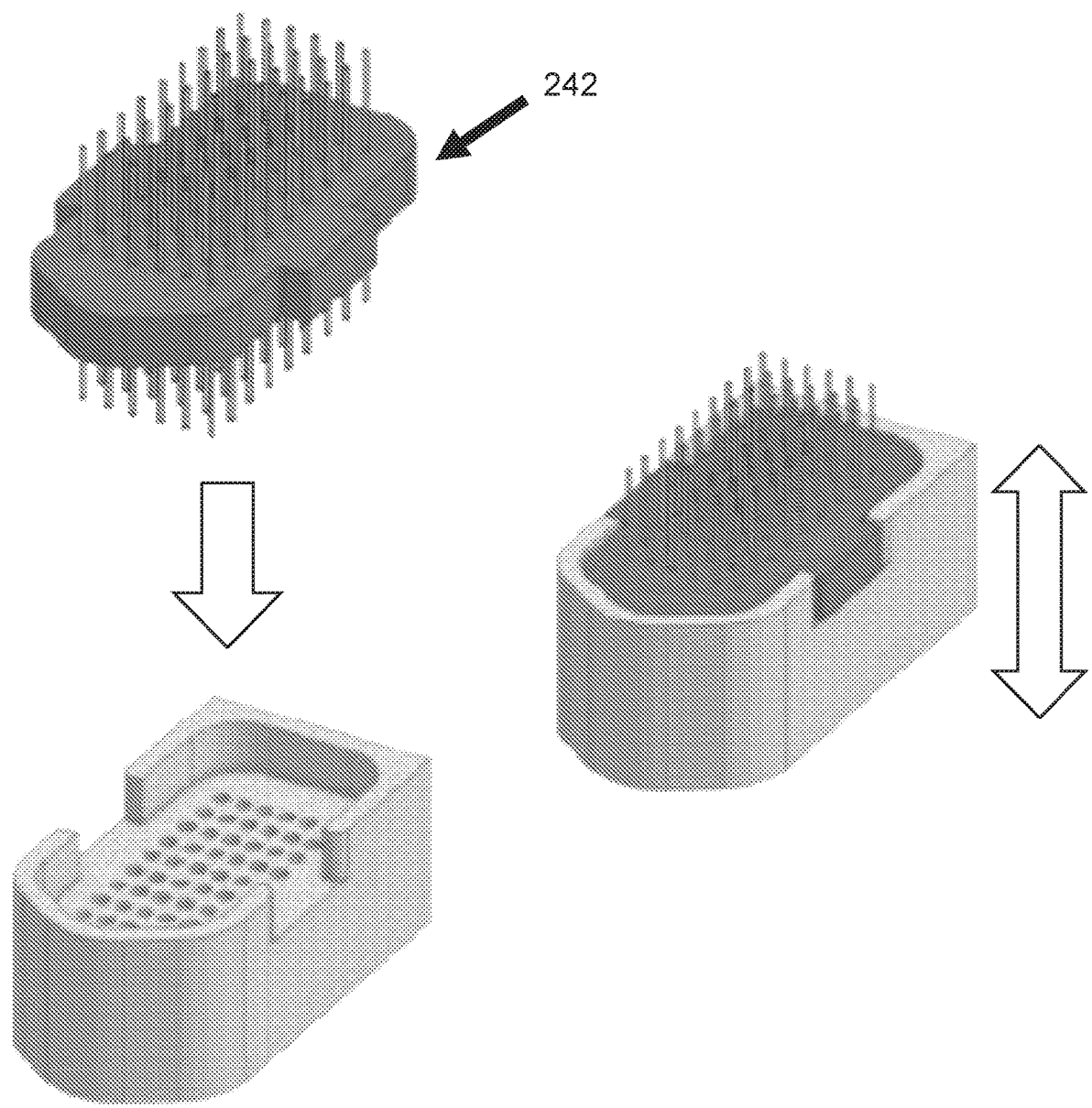
Figures 3, 7D:
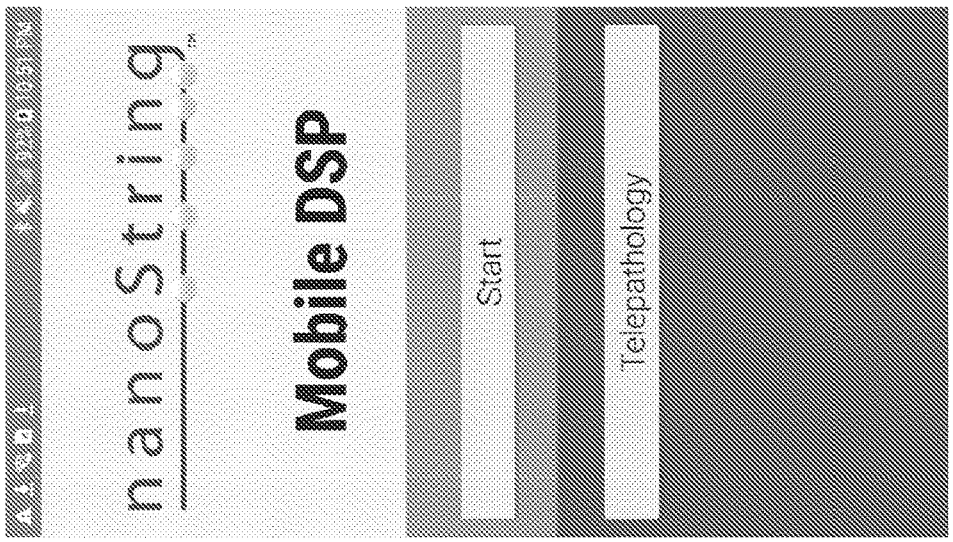
Figures 2, 7D:
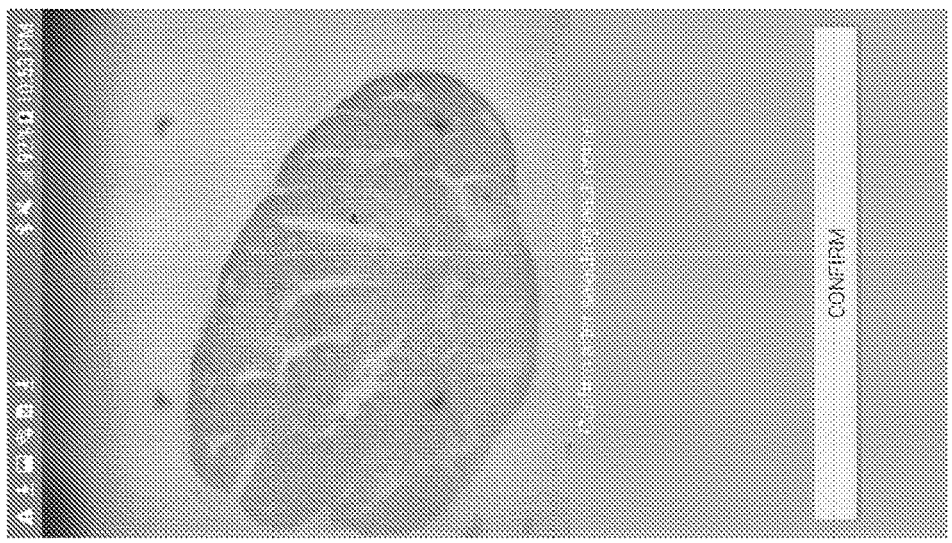
Figures 1, 7D:
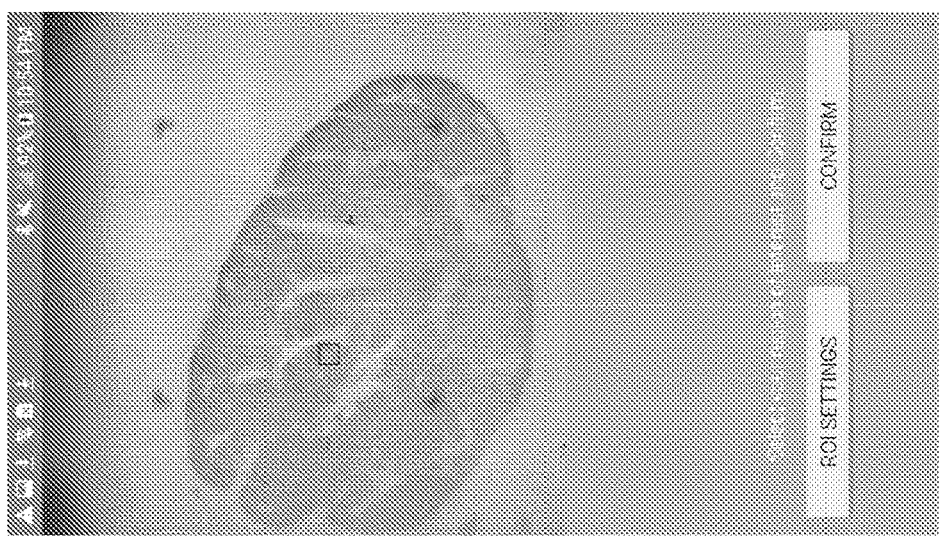
Figures 6, 7D:
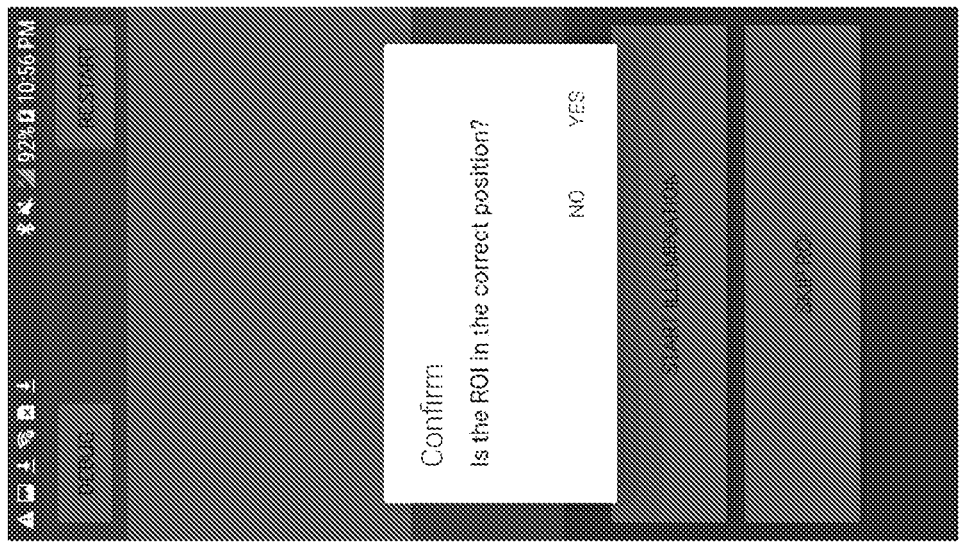
Figures 5, 7D:
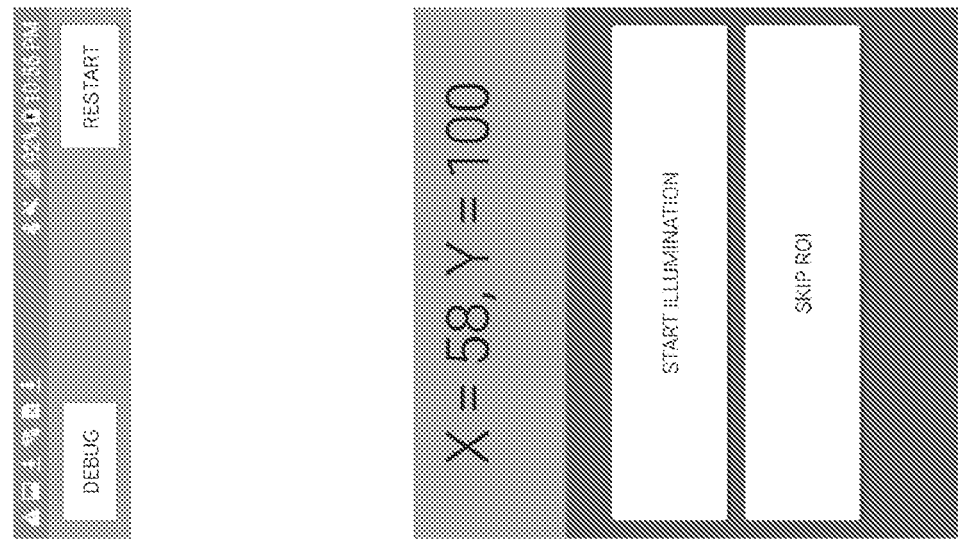
Figures 4, 7D:
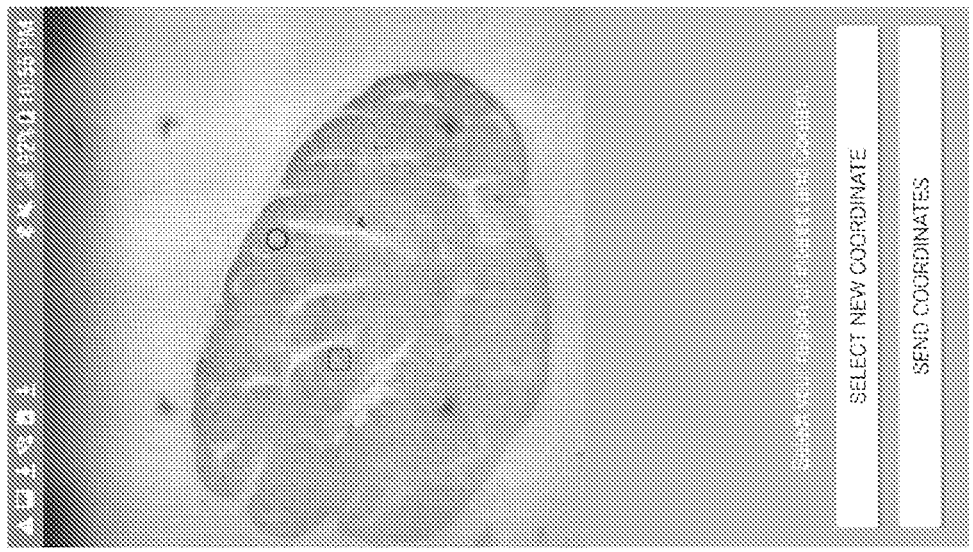
Figures 7, 7D:
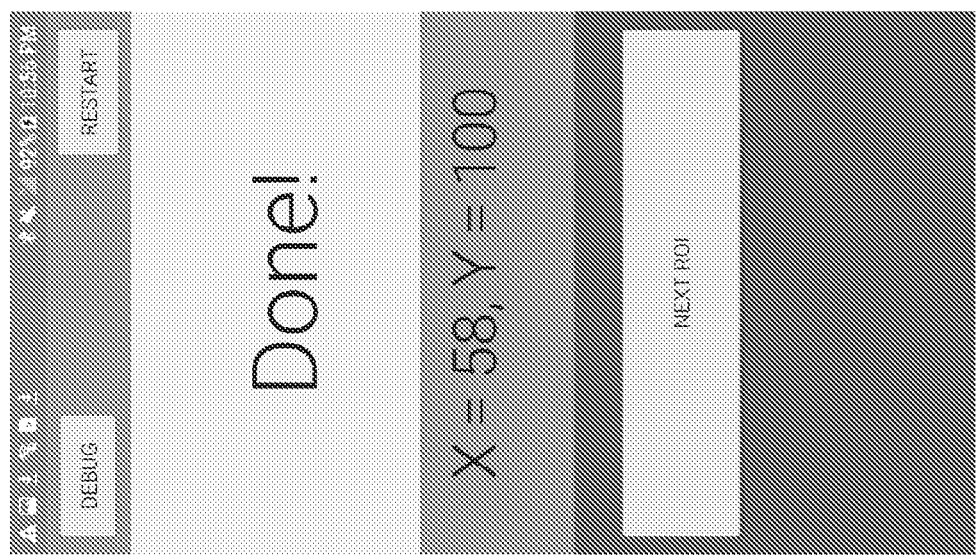

FIGS. 7D-1 through 7D-7, correspond to example screenshots for the GUI/software application according to some embodiments:

FIG. 7D-1: start GUI screenshot;
FIG. 7D-2: confirmation of corner selection screenshot;
FIG. 7D-3: confirmation of ROI screenshot;
FIG. 7D-4: selection of new coordinates and sending of coordinates screenshot;
FIG. 7D-5: initiation of illumination of selected ROI screenshot;
FIG. 7D-6: confirmation of correct ROI position screenshot; and/or (depending upon the embodiment)
FIG. 7D-7: completion of ROI imaging and continuation onto a next ROI screenshot.

Figure 8:
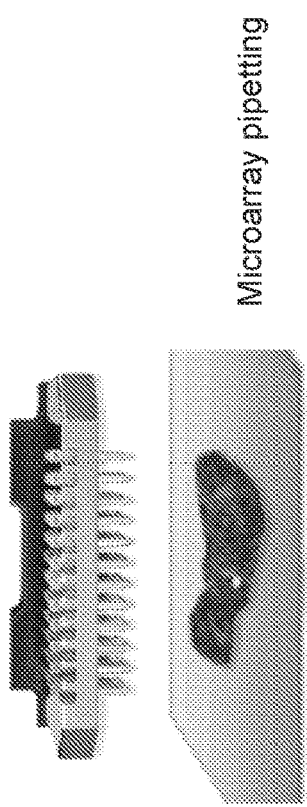
FIG. 8 illustrates a means for communicating fluid to/from tissue on a slide, in the DSP system according to some embodiments of the disclosure.
Figure 8:
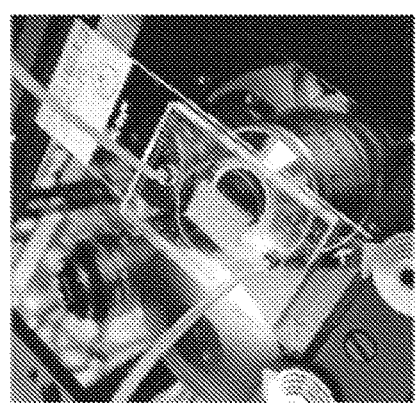
Figure 8:
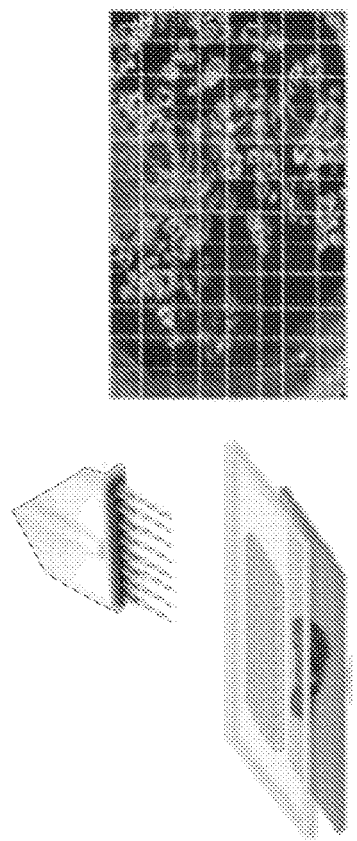
Figure 9A:
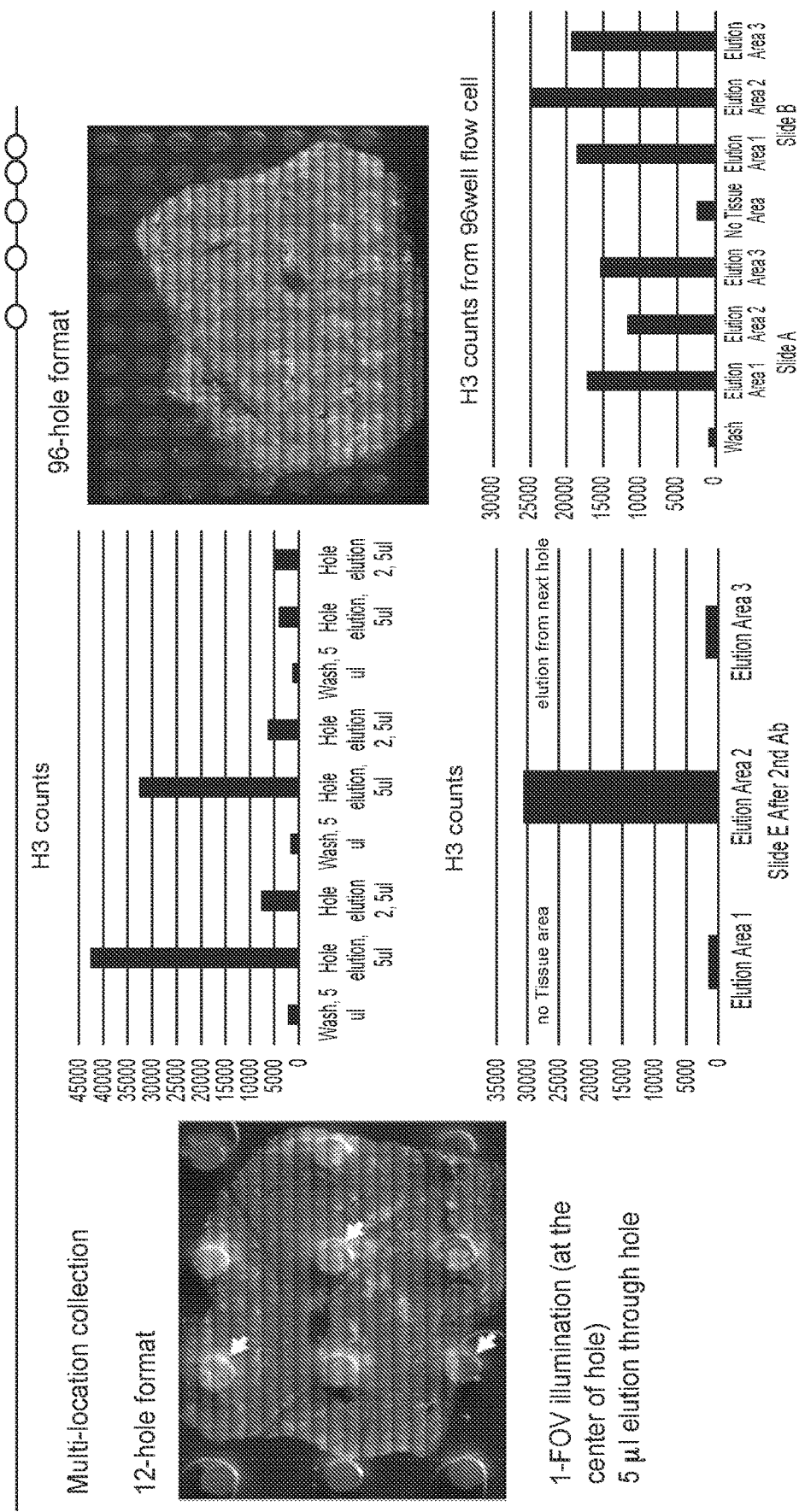
FIGS. 9A-C illustrates example patterns of openings, other structure, configurations and/or related data, for a DSP system according to some embodiments of the present disclosure.
Figure 9B:
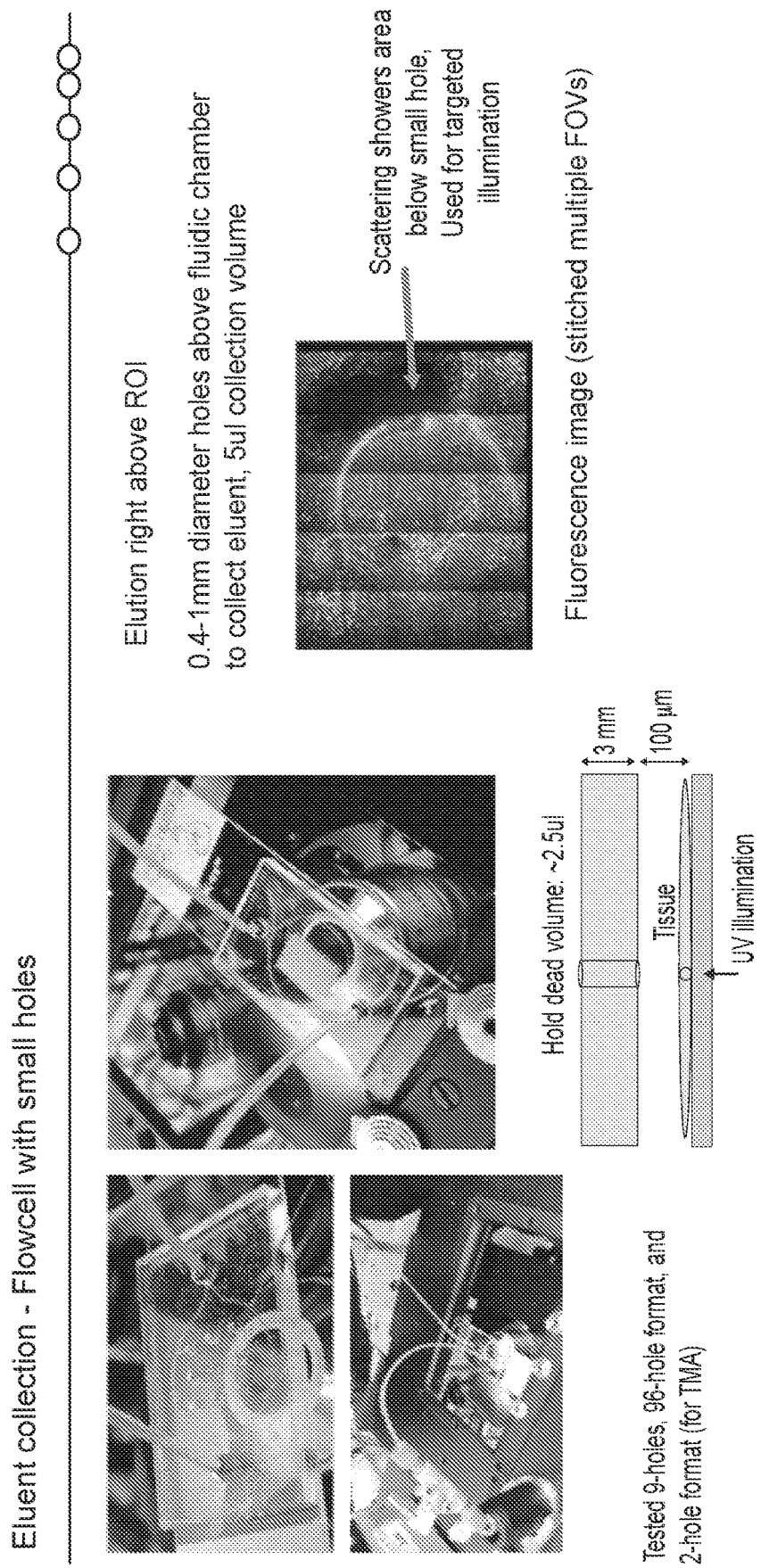
Figure 9C:
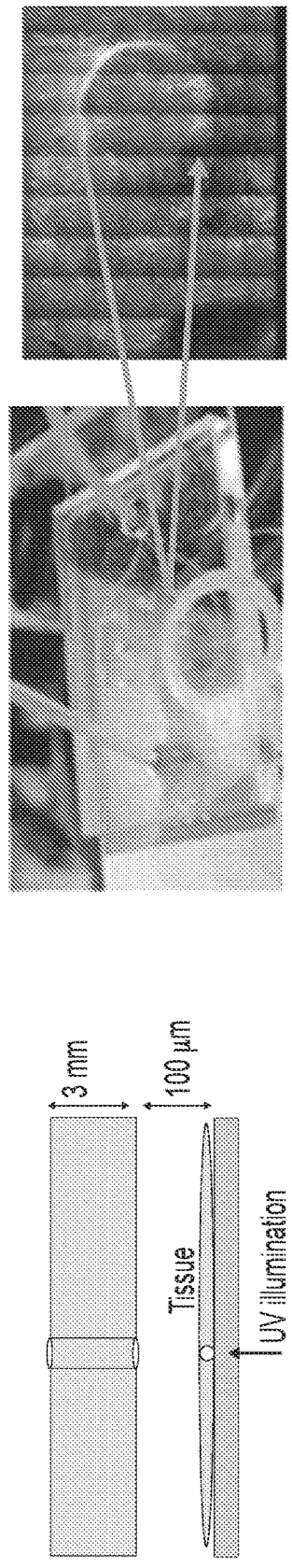
Figure 9C:
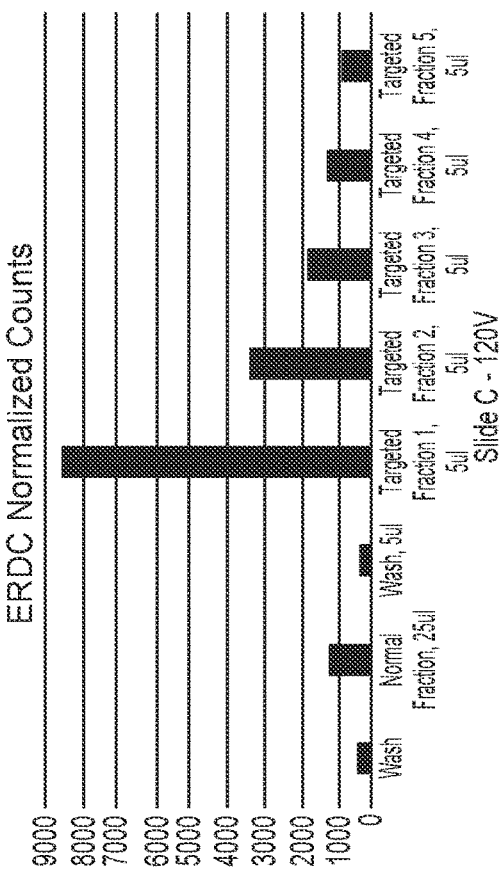

In some embodiments, structure and associated structure is provided to communicate fluid to and from the tissue on the slide. For example, as shown in FIG. 8, the cleaved oligos are aspirated, which can be done manually or via machine/robotically, via pipetting. Such can be conducted via openings/holes provided above the tissue sample/slide (and/or as part of the chamber, e.g., at least a portion thereof), or via, e.g., a flowcell. Guide means can be configured within or proximate to a slide and gasket configuration including a capillary means for communicating fluid from the tissue on the slide (see, e.g., FIGS. 2E-4, 2E-5). FIGS. 9A-C illustrates example patterns of such openings, other structure, configurations and/or related data pertaining thereto. Such fluid related structure and/or functionality can also include a pump system configured to provide a flow of a solution to and/or from the slide (e.g., supplying buffer solution). The cleaved oligos can be aspirated manually or via machine/robotically, via pipetting through a guide means such as a grid barrier as illustrated in FIG. 8. The guide means can be configured within or proximate to a slide and gasket configuration as illustrated in FIG. 2E-3.

Figures 1, 2, 3, 10D:
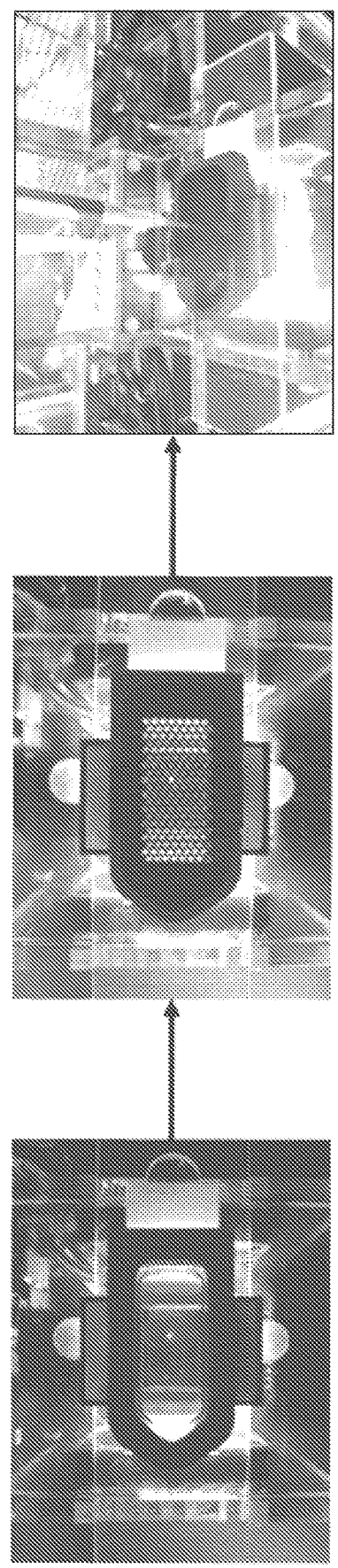

FIGS. 10A-10E-4 illustrates examples of fluid transport to/from a slide and/or an assay (e.g., 96 well plate), according to some embodiments of the present disclosure. For example FIG. 10A, illustrates a pipette guide 1005 for retrieving fluid (e.g., oligos) off a slide (for example). A perspective view of the guide is shown in FIG. 10B, as well as a top view in FIG. 10C. Points 1010 illustrate backlight from an LCD "opening", which illuminates corresponding array holes above a ROI, for guiding the pipette to a precise location. For example, FIGS. 10D-1 through 10D-3, show exemplary steps for collecting samples, including exposing the sample to white/visible light to visualize determined ROIs (FIG. 10D-1), inserting the guide and identifying the ROI location (FIG. 10D-2), and then inserting a pipette to retrieve the sample (FIG. 10D-3). This repeated for each ROI.

FIG. 10E-1 illustrate a micro-capillary array (e.g., 96 well format) 1010, with a guide 1020, over a sample 1030. FIG. 10E-2 illustrate the number of openings/holes to which the micro-capillary array can be used with above the sample. FIG. 10E-3 illustrates use of an airtight cap (for example) 1040, on the top of one or more capillary tubes, which can be a thin parafilm layer which can be removed by heat, a plug of photo degradable material, and/or a microfluidic valve. FIG. 10E-4 illustrates use of plugs 1050 on the bottom of one or more capillary tubes, which can be used in some embodiments to delay capillary action by a relatively short time period (e.g., several seconds or less), which can function so that no aspiration of fluid/sample occurs during UV illumination, but then can initiate immediately thereafter. Such a plug can comprise at least one of a layer of soluble material (e.g., salt, sugar), and a photo degradable layer (e.g., UV degradable).

While various inventive embodiments have been described and illustrated herein, those of ordinary skill in the art will readily envision a variety of other means, functionality, steps, and/or structures (including software code) for performing the functionality disclosed and/or obtaining the results and/or one or more of the advantages described herein, and each of such variations and/or modifications is deemed to be within the scope of the inventive embodiments described herein. More generally, those skilled in the art will readily appreciate that all parameters, and configurations described herein are meant to be exemplary and that the actual parameters, and configurations will depend upon the specific application or applications for which the inventive teachings is/are used. Those skilled in the art will recognize, or be able to ascertain using no more than routine experimentation, many equivalents to the specific inventive embodiments described herein. It is therefore to be understood that the foregoing embodiments are presented by way of example only and that, within the scope of any claims supported by this disclosure and equivalents thereto, inventive embodiments may be practiced otherwise than as specifically described and claimed. Inventive embodiments of the present disclosure are directed to each individual feature, system, apparatus, device, step, code, functionality and/or method described herein. In addition, any combination of two or more such features, systems, apparatuses, devices, steps, code, functionalities, and/or methods, if such features, systems, apparatuses, devices, steps, code, functionalities, and/or methods are not mutually inconsistent, is included within the inventive scope of the present disclosure. Further embodiments may be patentable over prior art by specifically lacking one or more features/functionality/steps (i.e., claims directed to such embodiments may include one or more negative limitations to distinguish such claims from prior art).

The above-described embodiments of the present disclosure can be implemented in any of numerous ways. For example, some embodiments may be implemented (e.g., as noted) using hardware, software or a combination thereof. When any aspect of an embodiment is implemented at least in part in software, the software code can be executed on any suitable processor or collection of processors, servers, and the like, whether provided in a single computer or distributed among multiple computers.

In this respect, various embodiments disclosed herein may be embodied at least in part as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium or non-transitory medium) encoded with one or more programs that, when executed on one or more computers or other processors, perform methods that implement the various embodiments of the technology discussed above. The computer readable medium or media can be transportable, such that the program or programs stored thereon can be loaded onto one or more different computers or other processors to implement various aspects of the present technology as discussed above.

The terms "program," "software," "code," or "software code" are used herein in a generic sense to refer to any type of computer code or set of computer-executable instructions that can be employed to program a computer or other processor to implement various aspects of the present technology as discussed above. Additionally, it should be appreciated that according to one aspect of this embodiment, one or more computer programs that when executed perform methods of the present technology need not reside on a single computer or processor, but may be distributed in a modular fashion amongst a number of different computers or processors to implement various aspects of the present technology, on and/or over a network.

Computer-executable instructions may be in many forms, such as program modules, or containers, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A digital spatial profiling (DSP) system comprising:
   a housing or other structure for containing at least one component of the DSP system, comprising:
      a power source;

an ultraviolet (UV) light source (UVS);
a visible light source (VLS) for bright field imaging;
a chamber comprising a slot configured to receive at least a portion of a slide having a tissue sample thereon;
a personal mobile computing device (PMD) comprising a user interface and a camera sensor, the PMD being arranged relative to the chamber in order to image the tissue sample on the slide within the chamber;
photomasking means configured to selectively illuminate the tissue sample with UV light from the UVS and/or visible light from the VLS;
optic means configured to at least one of direct and/or focus the UVS and/or VLS toward at least one of the tissue sample, the chamber, the photomasking means, and the camera sensor; and
processing circuitry configured to
acquire, via the camera sensor, an image of the tissue sample,
display, via the user interface of the PMD, the image of the tissue sample,
receive, via the user interface of the PMD, user input regarding a region of interest (ROI) of the tissue sample, and
illuminate, using the photomasking means, the ROI with UV light,
wherein the PMD is removably attachable to the housing and/or the chamber.

2. The system of claim 1, wherein:
the photomasking means comprises an LCD having a backlight, and wherein the VLS comprises the LCD backlight or external VLS,
the optics means comprises a first set for the UVS comprising a condenser lens or scan lens, a dichroic mirror, and a second set of optics comprising an objective lens,
the dichroic mirror is configured to redirect light from multiple sources into one optical axis;
the photomasking means comprises an LCD configured as a programmable aperture so as to structure at least one of UV light or visible light to reach the tissue sample only in the ROI;
and/or
the photomasking means comprises at least one of a digital micro-mirror device (DMD), a liquid crystal on silicon (LCoS) display, organic light-emitting diode (OLED), micro light-emitting diode (p LED) array, fiber optic bundle, a liquid crystal display (LCD), a scanning laser, and a physical barrier.

3. The system of claim 2, wherein:
the photomasking means comprises an LCD including a pixel grid, and wherein the LCD is arranged at a predetermined distance from the tissue sample;
the predetermined distance is configured such that the tissue sample is not obscured by the pixel grid;
the predetermined distance is selected to be between approximately 0.01 to 5 mm, 0.50 to 2.5 mm, 0.75 to 2.25 mm, or 1 to 2 mm; and/or
the predetermined distance is configured to provide clear visualization of the tissue sample, and/or to minimize diffusion of UV light.

4. The system of claim 1, wherein:
the system further comprises:
a pump system configured to provide a flow of a solution to the chamber, and/or
a software application operating on the processing circuitry and configured to cause the PMD to display, as the user interface, a graphical-user-interface (GUI) configured to receive the user input to select at least one ROI of the image acquired by the camera sensor and displayed via the user interface of the PMD, and
the photomasking means is configured to provide at least one of: an illumination resolution of between approximately 50 and 300 nm, a field of view between approximately 5-12 $cm^2$, and a magnification of between approximately 1-5×;
at least one of the housing, the chamber, and the slot is configured to receive and/or retrieve at least one solution,
the housing comprises or includes a plurality of scaffolds, a PMD frame, at least one objective lens frame, at least one slide frame, a photomasking frame, at least one condenser frame, and at least one thermal management means,
the housing is configured to removably receive a single objective lens frame of a plurality of objective lens frames each having a different objective lens and corresponding magnification, and/or
the system is further configured for at least one of dark-field microscopy, bright-field microscopy, phase-contrast microscopy, fluorescence microscopy and microscopy with ultraviolet surface excitation.

5. The system of claim 1, wherein
at least one of the housing, the chamber, and the slot are configured to enable the slide to move relative thereto, and/or
the housing, the chamber, and the slot is configured to receive and/or retrieve at least one solution.

6. The system of claim 5, wherein receiving and/or retrieving the at least one solution is via fluid transport.

7. The system of claim 6, wherein fluid transport comprises at least one of pipetting and capillary action, and wherein pipetting may be either manual or automatic via robotic means.

8. The system of claim 1, wherein the housing comprises or includes a plurality of scaffolds, a PMD frame, at least one objective lens frame, at least one slide frame, a photomasking frame, at least one condenser frame, and at least one thermal management means.

9. The system of claim 8, wherein the thermal management means comprises at least one of a heat sink, a heat pump, a fan, a liquid cooling system, and a peltier device.

10. The system of claim 1, wherein the housing is configured to removably receive a single objective lens frame of a plurality of objective lens frames each having a different objective lens and corresponding magnification.

11. The system of claim 10, wherein each objective lens frame is configured so as to provide a different spacing from the camera sensor.

12. The system of claim 1, wherein the PMD includes a PMD processor, a display, first wireless communication means for communicating information to a remote device either directly or via a network, and a second wireless communications means for communication with a local device.

13. The system of claim 1, further comprising a temperature sensor configured to determine the temperature in at least one of the housing and the chamber.

14. The system of claim 1, wherein the processor is configured to:

receive input from a temperature sensor corresponding to a sensed temperature, and to at least one of:

turn off the UVS upon the sensed temperature being greater than a predetermined temperature; and provide at least one of a visual and audible warning upon the sensed temperature being greater than a predetermined temperature.

15. The system of claim 1, further comprising:

sealing means to maintain a liquid environment over the tissue sample within the chamber, and/or manual fluid collection guiding means arranged proximate the tissue sample and configured to enable pipetting solution from the tissue sample.

16. The system of claim 15, wherein the manual fluid collection guiding means comprises a microarray configured as or with a flow cell and/or is arranged within or proximate to the chamber; and/or wherein the manual fluid collection guiding means comprises a grid barrier arranged within or proximate to the sealing means.

17. A digital spatial profiling (DSP) method comprising:

providing the system according to claim 1, wherein the processing circuitry is further configured to:

provide illuminating light to the tissue sample on the slide received within the slot of the chamber, wherein the tissue sample has previously been conjugated with an antibody solution and, prior to insertion, covered in a buffer solution, wherein the slide is received within the slot of the chamber for imaging and is aligned with the photomasking means;

image the tissue sample with the camera sensor of the PMD under visible light and display the image via the user interface of the PMD;

receive a selection of a plurality via the GUI, wherein the selection forms an outline of a rectangle;

define a ROI based on the selected plurality of biomarkers;

cease illuminating visible light; and expose the ROI of the tissue sample to UV light illumination for a predetermined period of time sufficient to cleave oligos in the ROI in the tissue sample, wherein the method further comprises collecting a solution from the tissue sample containing cleaved oligos.

18. The method of claim 17, wherein the processing circuitry is further configured to:

image the photomasking means prior to receipt of the slide so as to calibrate the photomasking means photomask, and/or change the size of the rectangle outlined by the selected markers.

19. A non-transitory computer readable medium having stored thereon instructions for enabling one or more computer processors to conduct one or more steps of the method of claim 17.

* * * * *

UNITED STATES PATENT AND TRADEMARK OFFICE
CERTIFICATE OF CORRECTION

| | | |
|---|---|---|
| PATENT NO. | : 12,002,572 B2 | Page 1 of 1 |
| APPLICATION NO. | : 17/413674 | |
| DATED | : June 4, 2024 | |
| INVENTOR(S) | : Joseph M. Beechem et al. | |

It is certified that error appears in the above-identified patent and that said Letters Patent is hereby corrected as shown below:

In the Claims

At Column 15, Claim number 1, Line number 25:
"regarding a region of interest (ROD of the tissue"
Should read:
--regarding a region of interest (ROI) of the tissue--

At Column 15, Claim number 2, Line number 49:
"(OLED), micro light-emitting diode (p LED) array,"
Should read:
--(OLED), micro light-emitting diode (µLED) array,--

At Column 18, Claim number 17, Line number 6:
"receive a selection of a plurality via the GUI, wherein the"
Should read:
--receive a selection of a plurality of biomarkers via the GUI, wherein the--

Signed and Sealed this
Ninth Day of July, 2024

Katherine Kelly Vidal
*Director of the United States Patent and Trademark Office*